United States Patent
Boucher et al.

(10) Patent No.: US 8,108,068 B1
(45) Date of Patent: Jan. 31, 2012

(54) PRESCRIPTION MEDICATION CONTROL SYSTEM AND METHOD

(76) Inventors: Gary R. Boucher, Shreveport, LA (US); Jonathan Glass, Shreveport, LA (US)

( * ) Notice: Subject to any disclaimer, the term of this patent is extended or adjusted under 35 U.S.C. 154(b) by 460 days.

(21) Appl. No.: 12/345,580

(22) Filed: Dec. 29, 2008

Related U.S. Application Data

(60) Provisional application No. 61/009,237, filed on Dec. 27, 2007.

(51) Int. Cl.
*G06F 17/00* (2006.01)
(52) U.S. Cl. .......................... 700/236; 700/240
(58) Field of Classification Search .................. 700/236, 700/240
See application file for complete search history.

(56) References Cited

U.S. PATENT DOCUMENTS

| | | | |
|---|---|---|---|
| 4,460,106 A | 7/1984 | Moulding | |
| 4,473,884 A | 9/1984 | Behl | |
| 4,662,537 A | 5/1987 | Wolf | |
| 4,869,392 A | 9/1989 | Moulding | |
| 5,042,685 A | 8/1991 | Moulding | |
| 5,097,429 A | 3/1992 | Wood et al. | |
| 5,200,891 A | 4/1993 | Kehr et al. | |
| 5,337,919 A * | 8/1994 | Spaulding et al. ................. | 221/2 |
| 5,809,997 A | 9/1998 | Wolf | |
| 6,148,815 A | 11/2000 | Wolf | |
| 6,539,281 B2 * | 3/2003 | Wan et al. ..................... | 700/236 |
| 6,771,174 B2 * | 8/2004 | Broas .......................... | 340/573.1 |
| 7,118,007 B1 | 10/2006 | Yates et al. | |
| 7,170,823 B2 | 1/2007 | Fabricius et al. | |
| 7,668,620 B2 * | 2/2010 | Shoenfeld ..................... | 700/237 |
| 7,689,318 B2 * | 3/2010 | Draper .......................... | 700/236 |
| 7,801,745 B2 * | 9/2010 | Walker et al. .................... | 705/2 |
| 2001/0019065 A1 | 9/2001 | William et al. | |
| 2002/0027507 A1 | 3/2002 | Yarin et al. | |
| 2002/0067270 A1 | 6/2002 | Yarin et al. | |
| 2002/0113077 A1 | 8/2002 | Topliffe et al. | |
| 2003/0024943 A1 | 2/2003 | MacDonald | |
| 2006/0154642 A1 | 7/2006 | Scannell, Jr. | |
| 2006/0215495 A1 | 9/2006 | Soled et al. | |
| 2007/0043469 A1 | 2/2007 | Draper | |
| 2007/0050271 A1 | 3/2007 | Ufford et al. | |
| 2008/0054007 A1 | 3/2008 | Mador | |
| 2008/0093448 A1 | 4/2008 | de la Huerga | |
| 2008/0114490 A1 | 5/2008 | Jean-Pierre | |
| 2008/0264967 A1 | 10/2008 | Schifman et al. | |

OTHER PUBLICATIONS

"Remote Monitoring of Health Conditions", IBM Research: Press Resources, printed Dec. 2008.
Lucas Conley, "A Pill With Brains", FastCompany.com, Dec. 7 <http://www.fastcompany.com/magazines/84/jetsons.htms>.
"Medicom: Leader in Drug Delivery Devise Solutions to help Patient Compliance—Tablet Reminders", <http://www.medicom.bang-olufsen.com/sw431.asp>, printed Dec. 2008.

(Continued)

*Primary Examiner* — Timothy Waggoner
(74) *Attorney, Agent, or Firm* — Raymond G. Areaux; Ian C. Barras; Carver, Darden, Koretzky, Tessier, Finn, Blossman & Areaux, LLC

(57) ABSTRACT

A medication dispensing device comprising a housing having an enclosure configured to provide direct access to a current medication container storing medication to be dispensed. The device includes a plurality of bins, each bin configured to receive and store therein a medication container within a bin seat. Additionally, the device includes a scale assembly, within the housing, configured to automatically lift the medication container from the bin seat, weigh the medication container at least once and lower the medication container into the bin seat during a weighing cycle.

195 Claims, 19 Drawing Sheets

OTHER PUBLICATIONS

"Anti-RFID Tags Protect Privacy", Data Centre World, Feb 25, 2004, <http://news.zdnet.co.uk/communications/0,1000000085,39147338,00.htm>.

Takacs and Hanak, "A Prototype Home Robot with an Ambient Facial Interface to Improve Drug Compliance", Journal of Telemedicine and Telecare, 2008, v 14: 393-395.

M. McGee, "Web Technology Helps Ensure Patients Take Their Medicine", Information Week, Dec. 2004, <http://www.informationweek.com/shared/printableArticleSrc.jhtml?articleID=55301175>.

Dawn Kawamoto, "Managing the Meds from Miles Away", CNET News, < http://news.cnet.com/Managing-the-meds-from-miles-away/2100-11393_3-6188642.html>, Jun. 5, 2007.

Diane Dannenfeldt, "How Prescription Alerts Work", How Stuff Works, <http://communication.howstuffworks.com/prescription-alerts3.htm>, printed Dec. 2008.

The MedCenter Systems, MedCenter Store, <http://www.rnedcentersystems.com/zMedCenterSystem.html>, printed Dec. 2008.

Parkinson Timer and Alarm for Better Parkinson's Disease Care: Pill Dispenser, Vibrating Alarm Pill Timer, <http://www.medclock.com>, printed Dec. 2008.

Pill Bottle Multi Alarm Timer for Insulin and Pills, <http://www.medicalwatches.com/thepilltimer.html>, printed Dec. 2008.

Timex Healthcare—timex Nutrition Manager and Timex Daily Medication Manager, <http://www.timexhealthcare.com/managers.html>, printed Dec. 2008.

* cited by examiner

PRESCRIPTION MEDICATION CONTROL SYSTEM AND METHOD

CROSS-REFERENCE TO RELATED APPLICATIONS

The present application claims priority from U.S. Provisional Application No. 61/009,237, filed Dec. 27, 2007, which is incorporated herein by reference as if set forth in full below.

BACKGROUND OF THE INVENTION

1. Field of the Invention

The present invention relates generally to a control system for medication dispensation. Further, the present invention relates to a control system that monitors the dosage of prescription medicine.

2. Background of the Invention

It is our understanding that elderly patients have become the largest consumer of prescription medicines; however, we speculate that deteriorating eyesight, lapsed memory, or general forgetfulness associated with old age sometimes make regular intake of medication difficult. We speculate that patients have to remember which medicines to take, how much of a particular medication is needed, and at what times the medication needs to be taken. In addition, we speculate that patients need to remember whether to swallow or chew a pill, whether to take a medication with water or food, and whether to avoid taking a particular medicine with other medications. Consequently, we speculate that management of medication can be a daunting task with little room for error for not only the elderly, but for any person or pharmaceutical retailer.

In particular, we speculate that the dosage amount of a medication is critical and can have debilitating effects if not carefully monitored. We speculate that taking too little of a medication may not provide enough of that medicine to have a desired effect. On the other hand, we speculate that taking too much of a medication may have undesirable effects. We speculate that unintentional overdoses of medications have increased in recent years due to several factors including the greater accessibility to medications, the increasing practice of prescribing more medication, and the constantly-growing and ever-changing pharmaceutical market.

It has been reported that the World Health Organization estimates that only about 50% of patients typically take their medications as prescribed. It has been further reported that, in the United States, non-adherence affects patients of all ages and genders and is just as likely to involve higher income, well-educated people as those at lower socioeconomic levels. It has been further reported that an estimation of more than 125,000 people die each year due to prescription medication non-compliance, twice the number killed in automobile accidents. It has been further reported that everyday, prescription medication non-compliance costs an estimated $270 million in additional hospitalization and other medical costs, and that approximately 9 out of 10 outpatients take their medications improperly which contributes to prolonged and additional illness. It has been further reported that people who miss dosages need approximately three times as many doctor visits as others and face increased medical costs.

It has been reported that, at any given time, regardless of age group, it is estimated that up to 59% of individuals on five or more medications are in non-compliance, and that ten percent (10%) of all hospitalization are the result of prescription medication non-compliance. It has also been reported that 23% of all nursing home admissions are due to a failure to take medications properly. It has also been reported that approximately one-third of all patients take their prescribed medications, one-third of patients take some of the medication as prescribed, and one-third do not even fill their prescription.

Thus, there remains a need for a prescription medication control system that accurately monitors medications to ensure an appropriate dosage of a prescribed medicine is taken, thereby preventing adverse effects.

SUMMARY OF THE INVENTION

Techniques to control dispensing of medications and track a patient's adherence to a dispensing schedule are provided.

The present invention is directed to a medication dispensing device comprising a housing having an enclosure configured to provide direct access to a current medication container storing medication to be dispensed. The device includes a plurality of bins, each bin configured to receive and store therein a medication container within a bin seat. Additionally, the device includes a scale assembly, within the housing, configured to automatically lift the medication container from the bin seat, weigh the medication container at least once and lower the medication container into the bin seat during a weighing cycle.

According to the present invention, during the weighing cycle the scale assembly lifts the medication container from the bin seat, weighs the medication container, and then lowers the medication container into the bin seat. Multiple repetitions of the physical act of weighing using the above-described technique, where results of each act of weighing are averaged together, would improve accuracy but cost time as it may require up to several seconds to raise and lower the container to perform each weighing operation. Thus, an alternative to repeated physical weighing would be to raise the container once and capture (or sample) multiple, discrete readings from the output of the weight sensor (perhaps 256 times) and then average the captured discrete readings by taking the sum of said readings and dividing by the number of samples taken. This approach should, we speculate, reduce random noise in the system which tends to affect electronic weighing devices.

In the present invention the device includes a primary lid and a secondary dispensing lid wherein during the dispensing cycle, the primary lid is in a locked state and the secondary dispensing lid is configured to be automatically unlocked and either manually or automatically moved (lifted) to an open position.

The device according to the present invention includes a rotatable medicine carousel configured to rotate the medicine container in a respective one bin, said container having the medication to be dispensed, to a dispensing position immediately below the secondary dispensing lid prior to automatically moving the secondary dispensing lid to the open position.

The device according to the present invention disables the scale assembly and the rotatable medicine carousel when the primary lid is open.

The device according to the present invention includes a radio frequency identification (RFID) tag reader configured to read RFID data associated with an RFID tag affixed to the medication container.

The device according to the present invention includes a communication module configured to communicate the RFID data to a website and to receive a dispensing trigger signal from the website according to a determined dispensing schedule for the medication. The dispensing trigger identifies and initiates a dispensing sequence of a respective one medication in a respective one bin.

The device according to the present invention includes a processor configured to cause the rotatable medicine carousel to align the respective one bin to the dispensing position and to cause the secondary dispensing lid to be unlocked.

The device according to the present invention includes a sensor configured to determine the presence of the medication container being returned to or removed from the bin seat.

The present invention includes in one configuration a system comprising a plurality of in-home medication dispensing and control (MDC) devices, each MDC device having a secure housing configured to store therein a plurality of registered medication containers in discrete bin locations, and a scale assembly configured to weigh one medication container at a time. The system includes a server (for example, a computer) configured to register and track an amount of dosage taken based on a weight generated by the scale assembly for each registered medication associated with each MDC device.

Figure 1:
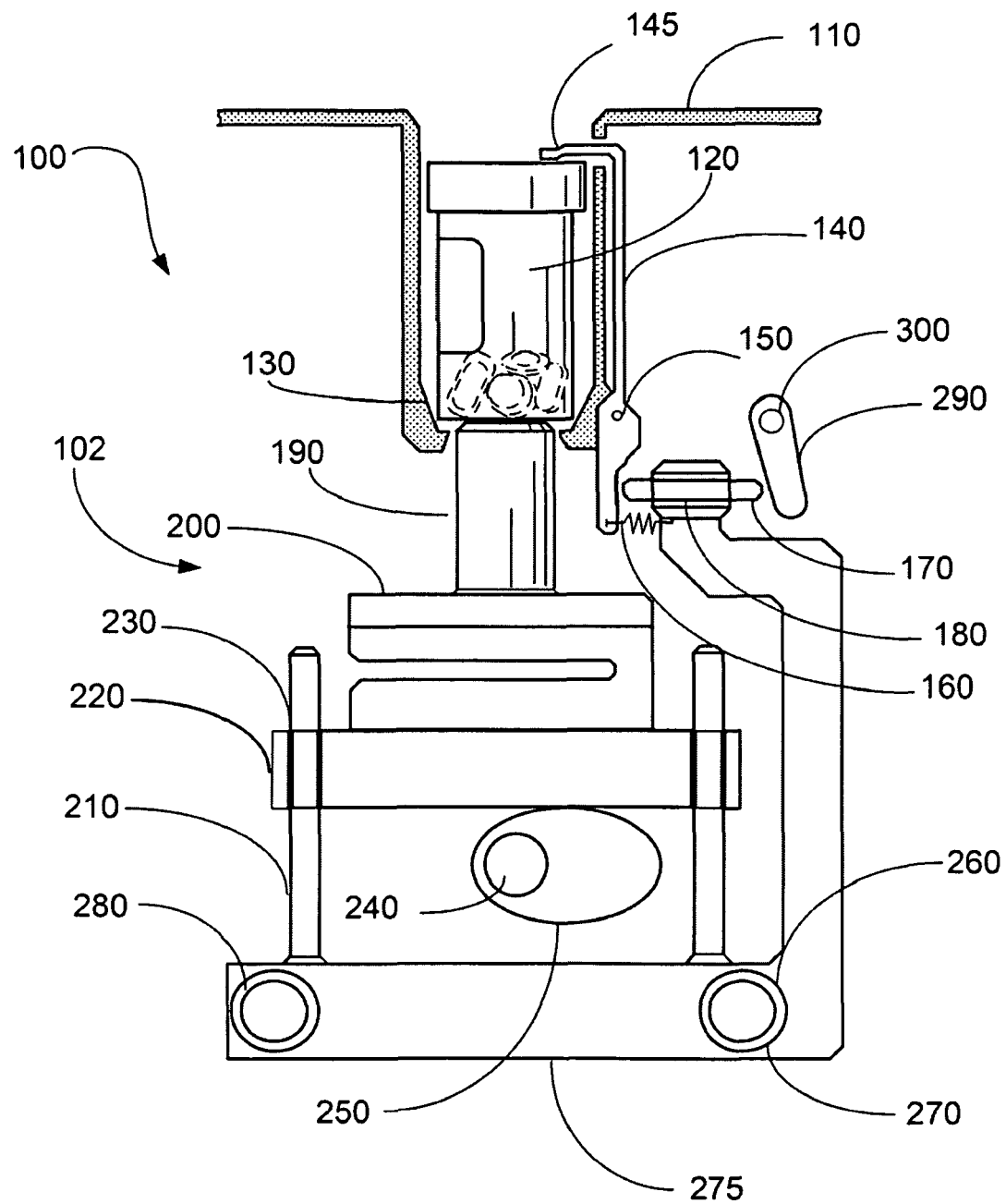
FIG. 1 is a weighing assembly of an in-home medication dispensing and control (MDC) device according to one embodiment of the present invention.

To facilitate understanding, identical reference numerals have been used, where possible, to designate identical elements that are common to the figures, except that suffixes may be added, when appropriate, to differentiate such elements. The images in the drawings are simplified for illustrative purposes and are not depicted to scale. It is contemplated that features may be beneficially incorporated in other configurations without further recitation.

Also in the following description, it is to be understood that such terms as "forward," "rearward," "front," "back," "right," "left," "upwardly," "downwardly," and the like are words of convenience and are not to be construed as limiting terms.

The appended drawings illustrate exemplary configurations of the disclosure and, as such, should not be considered as limiting the scope of the disclosure that may admit to other equally effective configurations.

DETAILED DESCRIPTION

The word "exemplary" is used herein to mean "serving as an example, instance, or illustration." Any configuration or design described herein as "exemplary" is not necessarily to be construed as preferred or advantageous over other configurations or designs, and the terms "core", "engine", "machine", "processor," "microcontroller" and "processing unit" are used interchangeably.

The techniques described herein may be used for controlling medication dispensation to a user. However, the techniques are also suited for monitoring medications dispensed from a pharmacy, or other controlled substances in other environments or industries.

The present invention provides an apparatus for use in a prescription medication control system for monitoring the dosage of a prescribed medicine including a medication container housing; a load cell; an actuator that positions medication containers or positions the load cell; a lock-out system having an elevator; a medication information storage center; and a communication mechanism; wherein the apparatus is used in a home, pharmacy, or other location for providing an appropriate medication dosage and transmitting dosage information to the user and to a third party at a remote location.

The present invention also provides a complete system for monitoring the dosage and usage of a prescribed medicine including a medication container housing; a load cell; an actuator that positions medication containers or positions the load cell; a lock-out system having an elevator; a medication information storage center; and a communication mechanism; wherein the lock-out system prevents a user from obtaining an incorrect medication or an incorrect amount of medication; and wherein the communication mechanism may warn the user or a third party of an incorrect dosage; thereby providing a system for preventing users from ingesting an inappropriate amount of a prescribed medication. If a patient takes an incorrect amount of medication, such as an overdosage, said overdose would be detected once the container was returned to its bin and was reweighed. As a result of such detection, the patient would be locked out from taking such medication for a predetermined time or an administration reset may be necessary.

In addition, the present invention provides methods for controlling prescription medication, in particular in situations where doses of a medication need to be monitored, the methods include the steps of providing an apparatus to monitor the dosage of a prescription medicine having a medication container housing; a load cell; an actuator that positions medication containers or positions the load cell; a lock-out system having an elevator; a medication information storage center; and a communication mechanism; wherein the system functions to protect the user from taking an incorrect dosage of a medication, including warning the user or a third-party when an incorrect dosage of a medication has been taken.

Medication Dispensing and Control (MDC) Device

Referring now to the drawings in general, the illustrations are for the purpose of describing an embodiment of the invention and are not intended to limit the invention thereto. As best seen in FIG. 1, a weighing assembly 102 of a medication dispensing and control (MDC) device 100, constructed according to one embodiment of the present invention, is shown. The MDC device 100 monitors the dosage and usage of prescription medication.

The MDC device 100 in FIG. 1 is an apparatus that a user places on a flat surface such as a counter or table to monitor the dosage of dispensed prescribed medicine. Medication container housing 110 holds medication containers 120 in a receptacle well 130. Preferably, the medication containers 120 are standard-sized pharmaceutical bottles, but a stepped narrowing of the receptacle well 130 could accommodate medication containers 120 of different sizes. The receptacle wells 130 can be of varying sizes to accommodate for larger or smaller medication containers.

Figure 2:
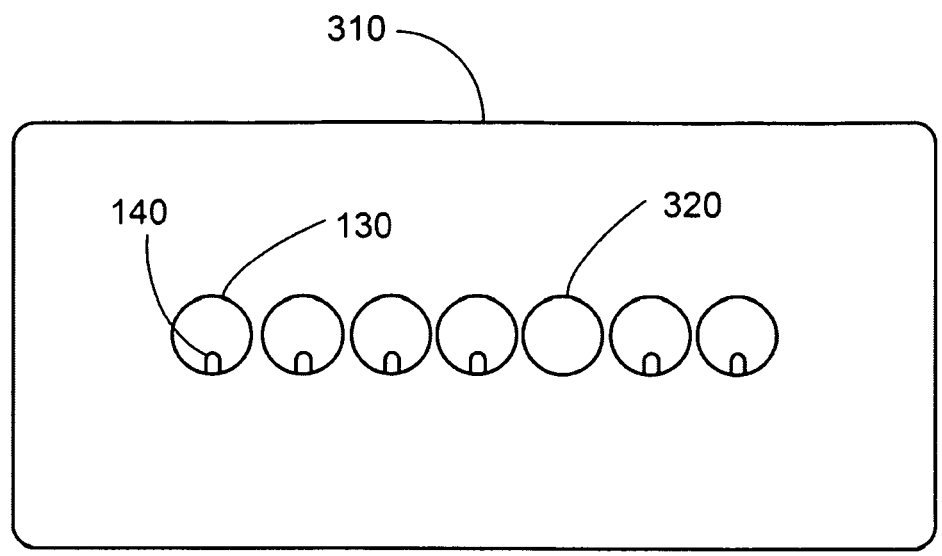
FIG. 2 is a top view of the linear medication dispensing rack of the MDC device, in accordance with one embodiment of the present invention.

FIG. 2 is a top view of a linear medication container housing 310 of one embodiment of the medication container housing 110 in FIG. 1. Medication containers 120 in FIG. 1 rest in receptacle wells 130 in FIGS. 1 and 2. The medication containers 120 are held in place by retainers 140 in FIGS. 1 and 2 that partially cover the tops of the medication containers 120. The tabs 145 of the retainers 140 preferably may be about 0.5 inches in length. Alternatively, gripping mechanisms could be used on the bottom of medication containers 120 to hold them in place. The retainers 140 also serve as lock-out mechanisms, making only one particular medication container 120 available at an appropriate time. Receptacle well 320 in FIG. 2 shows the retainer 140 retracted, allowing the user to access the medication container 120 in that particular receptacle well 130. Covered or internal receptacle wells can house calibration weights rather than medication containers 120 if needed. The calibration weights may be made of brass or a similar material that is resistant to corrosion.

Figure 3:
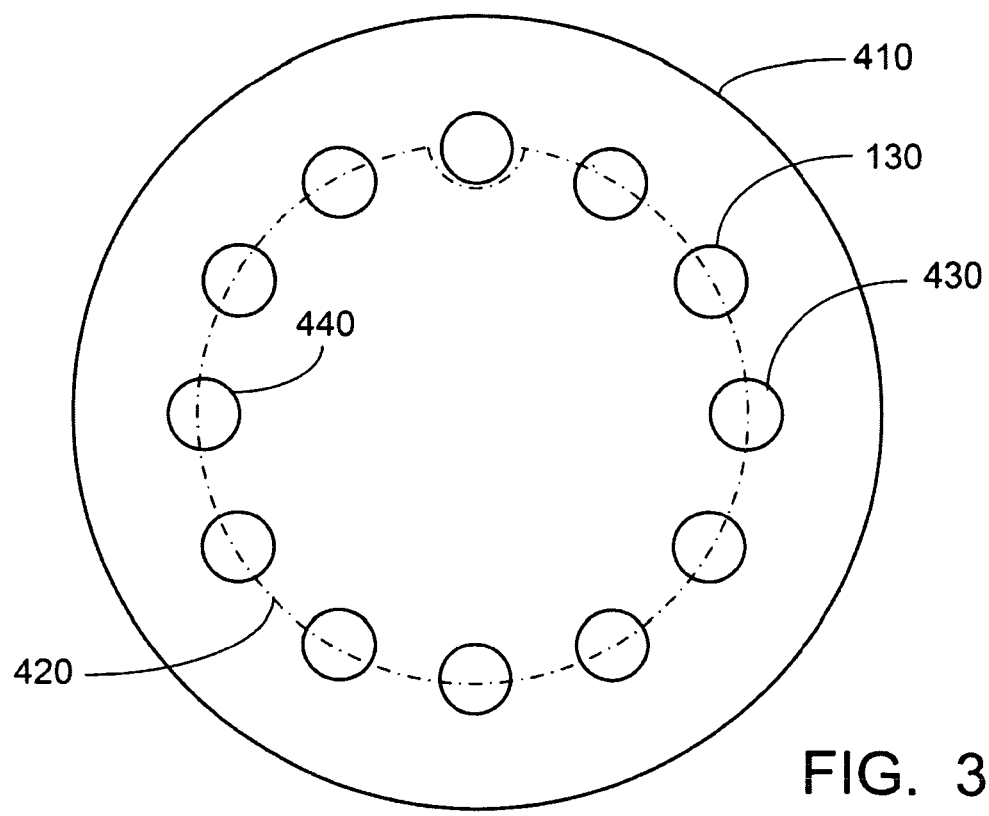
FIG. 3 is a top view of a rotary medication dispensing carousel of the MDC device, in accordance with one embodiment of the present invention.

FIG. 3 is a top view of a rotary medication dispensing carousel 410 for use in the MDC device 100. Rotary medication dispensing carousel 410 in FIG. 3 is another embodiment of the medication container housing 110 in FIG. 1 and is designed similar to a carousel. Medication containers 120 in FIG. 1 rest in receptacle wells 130 in FIGS. 1 and 3. The rotary medication dispensing carousel 410 can be rotated to position a particular medication container 120 for delivery to the user. Rotary locking mechanism 420 in FIG. 3 serves as a lock-out mechanism, only making one particular medication container 120 available at an appropriate time. When no medication is needed, the slot in the rotary locking mechanism 420 can be positioned to one or more possible locations having no receptacle well 130. If needed, any two opposite receptacle wells, such as receptacle wells 430 and 440, can house calibration weights instead of medication containers 120.

Once the medication container housing 110 in FIG. 1 is populated with one or more medication containers 120, MDC device 100 is able to both weigh the medication container 120 with its contents and deliver the correct medication container 120 by elevating it to an accessible position for the user. The MDC device 100 accomplishes these tasks by first centering each medication container 120 in its respective receptacle well 130 using a gradual tapering toward each well's bottom. The well's respective retainer 140 locks the medication container 120 in place and is hinged with a pin 150. A spring 160 holds the retainer 140 in a locked mode until retainer 140 is deactivated (unlocked) for dispensing.

The unlocking of a medication container 120 at a particular receptacle well location occurs with the aid of a plunger 170 on a linear bearing 180 that is activated by a lock-out cam 290. In one embodiment of the present invention, the lock-out cam 290 and its shaft 300 run the full length of the MDC device 100. The plunger 170, however, rides along with the main platform 275 on the lead screw 280 and rail 260 and allows only the particular receptacle well 130 corresponding to the position of the main platform 275 to unlock when the lock-out cam 290 is activated. The activation of lock-out cam 290 pushes the plunger 170 into the bottom of the retainer 140. This removes the top of the retainer 140 from the top of a medication container 120, allowing access to the medication container 120.

The main platform 275 is driven by a lead screw 280 and slides on a rail 260 that runs through a linear bearing 270. Four precision shafts 210 are mounted to the main platform 275 and allow a floating platform 220 to articulate vertically using linear bearings 230. The floating platform 220 is driven to various vertical positions by the position of an elevation cam 250 that is driven by a shaft 240. The elevation cam 250 and shaft 240 run the full length of the MDC device 100 and are functional at any receptacle well position.

Once the plunger 170 arrives at the receptacle well location corresponding with the position of the main platform 275, a load cell 200 that is connected to a pedestal 190 is elevated by the floating platform 220 to a position where the medication container 120 is supported solely by the pedestal 190 resting on the load cell 200. These two components serve to both weigh the medication container 120 and to elevate it for the user to remove. The weighing is done by the load cell 200, which is a force-sensing cell that has the ability to weigh one medication container 120 at a time. It is calibrated by two masses, a low-end weight and a high-end weight, to prevent calibration drift, where the MDC device 100 becomes less accurate. Recalibration is performed routinely and when necessary by an on-site or remote processor.

After weighing a medication container 120, the floating platform 220 is raised further via the elevation cam 250 to its full position, while the retainer 140 is retracted, allowing a user to lift the medication container 120 from the MDC device 100. Once the medication container 120 is replaced at a particular receptacle well position, the platform 220 is lowered to allow the pedestal 190 the freedom to move to the next receptacle well position for measurement or dispensing of the next medication container 120.

Figure 4:
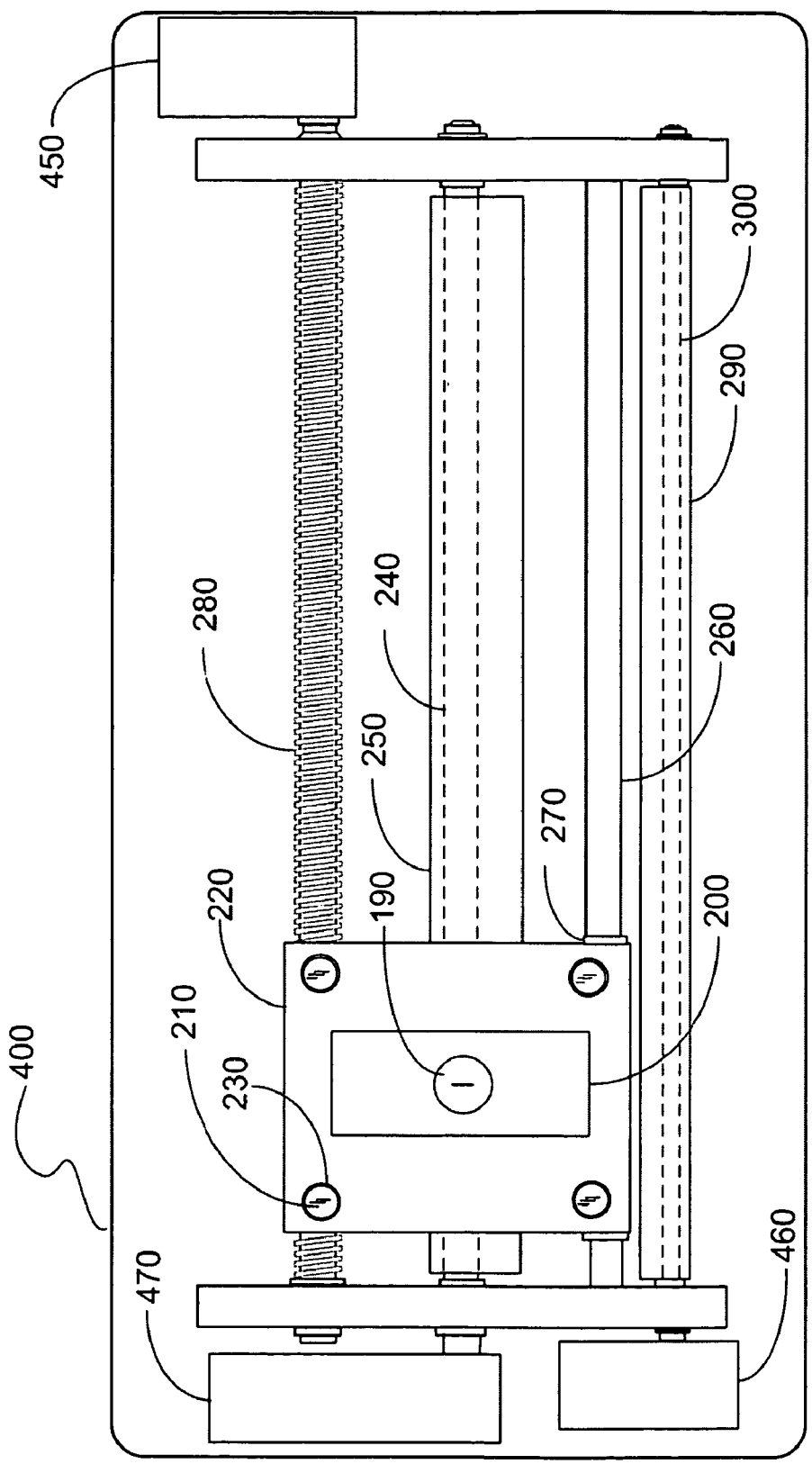
FIG. 4 is a top view of the linear actuation mechanism of the MDC device, in accordance with one embodiment of the present invention.

The actuation mechanism 400 in FIG. 4 that performs the aforementioned movements corresponds to the linear medication container housing 310 in FIG. 2. The position of the main platform 275 in FIG. 1 is controlled via the lead screw drive 450 in FIG. 4 that rotates the lead screw 280 in FIGS. 1 and 4. The lock-out cam 290 and elevation cam 250 in FIGS. 1 and 4 are operated by the lock-out cam drive 460 and the elevation cam drives 470 in FIG. 4. FIG. 4 also shows the pedestal 190 and the four vertical slide posts 210 with linear bearings 230 from a top view that are all present in FIG. 1. Linear bearings 270 for horizontal platform positioning are also illustrated in FIGS. 1 and 4. Preferably, in the case of a linear medication container housing 310 in FIG. 2, or a rotary medication dispensing carousel 410 in FIG. 3, the actuation mechanism 400 in FIG. 4 moves the platform and other weighing components under a particular receptacle well 130 in FIGS. 1, 2, and 3. Alternatively, the actuation mechanism 400 in FIG. 4 could move either of the two types of medication container housings 310 in FIGS. 2 and 410 in FIG. 3, while the platform and other weighing components remain stationary.

The MDC device 100 in FIG. 1 also has the ability to store medication information. Preferably, the MDC device 100 reads RFID tags that can easily store up to two kilobytes of data, and the tags would be placed on medication containers 120 at a pharmacy. Alternatively, the user could manually enter the medication information into the MDC device 100. Medications and their respective information could be represented with codes by compacting, compressing, or tokenizing the data. Furthermore, CRC (Cyclic Redundancy Check) error checking could verify that the data received is correct. Alternatively, bar codes or other types of identification technologies could be used in lieu of RFID. For example, a serial number (whether machine readable, manually entered or both) could be assigned to each medication container 120 to transmit back to a pharmacy or other remote location for identification and to assign the container to a specific patient.

Furthermore, the MDC device 100 in FIG. 1 has a means to communicate with a remote location via the Internet, landline telephone, mobile phone, M2M (Machine to Machine) system, etc. (these multiple means of communication being interchangeably referenced herein). The MDC device 100 is able to transmit medication information, dosage data, the amount of medication remaining, and any warnings concerning incorrect dosages or usage.

Figure 5:
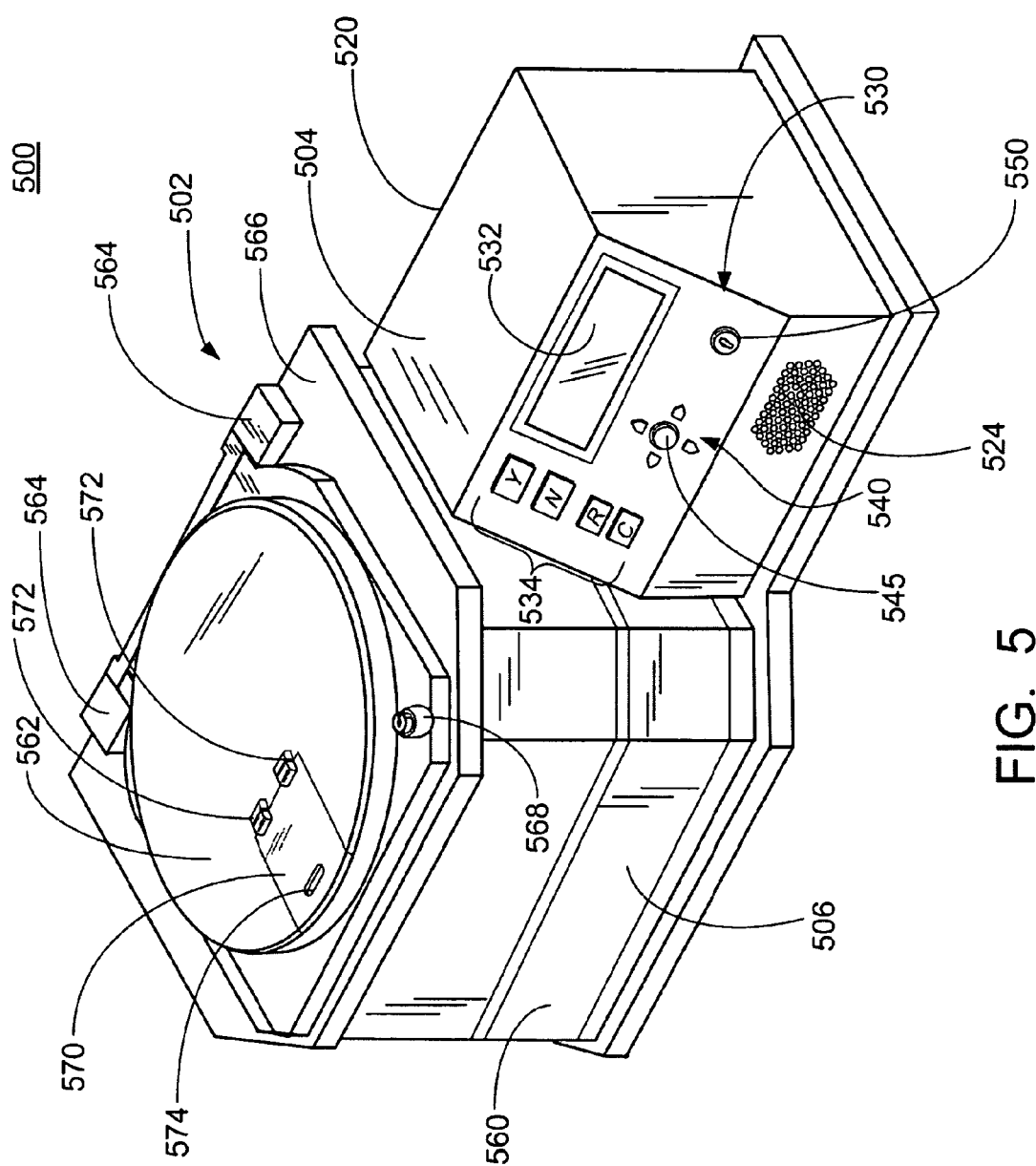
FIG. 5 is a perspective view of the in-home medication dispensing and control (MDC) device, in accordance with one embodiment of the present invention.
Figure 6:
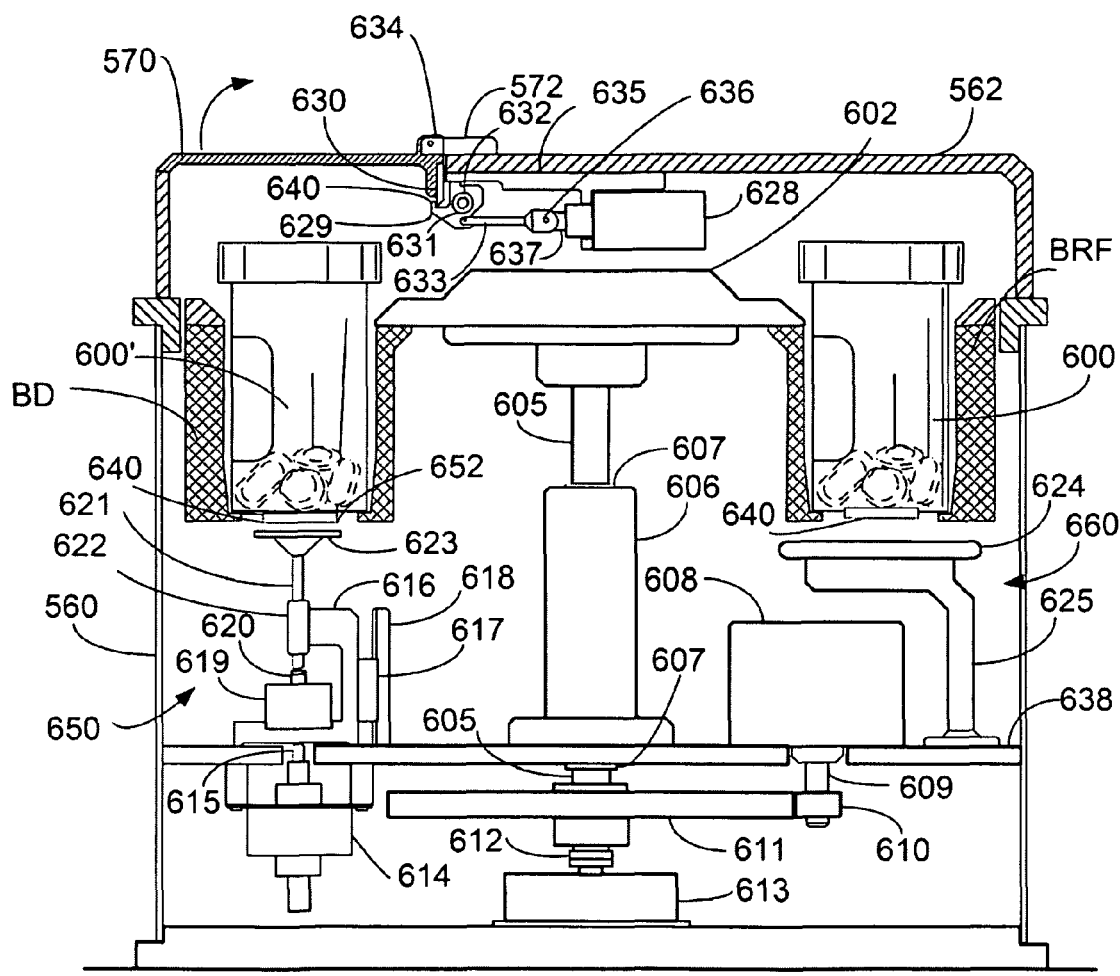
FIG. 6 is an interior cross-sectional view of the medication dispensing compartment 506 of the MDC device, in accordance with one embodiment of the present invention.
Figure 7A:
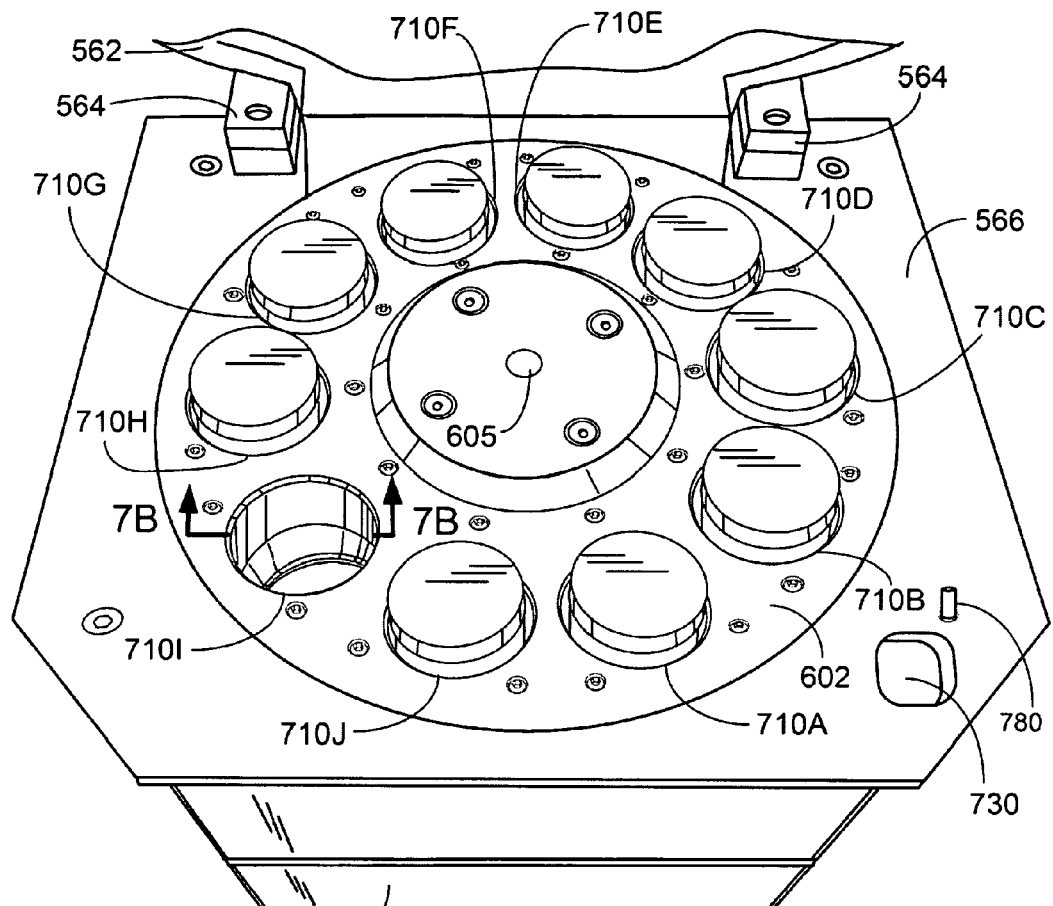
FIG. 7A illustrates a top elevational view of the medication dispensing compartment with the primary lid in an open position, in accordance with one embodiment of the present invention.

FIG. 5 is a perspective view of in-home medication dispensing and control (MDC) device 500. The MDC device 500 includes a housing 502 with first and second compartments 504 and 506. The compartment 504 houses a plurality of integrated circuits including one or more microcontrollers 802 (FIG. 8), memory 818, circuits of user interfaces (UI) 530, input/output ports (I/O) 835 (FIG. 8), etc., all of which is described in more detail in relation to FIG. 8. The compartment 506 houses and dispenses medications from a medication dispensing carousel 602, as best seen in FIGS. 6 and 7A. While two compartments are shown, the housing 502 may be a single compartment or multiple compartments.

The first compartment 504 is an enclosure 520 having a speaker grill 524 in one of the enclosure's walls and UI 530. UI 530 includes a display 532 and a first set of a plurality of control buttons 534. In one configuration, pushbutton switches are a preferred implementation of the plurality of control buttons 534; however, other switches types can be used. UI 530 further includes a second set of a plurality of control buttons 540. One or more of the control buttons of the first and second sets of the plurality of control buttons 534 and 540 are used for navigation through system menus and other information presented in a text format suitable for display or presentation using the display 532. One or more of the control buttons of the first and second set of control buttons 534 and 540 may have associated therewith a Braille legend (NOT SHOWN) to assist the visually impaired. The Braille legend may be below the control button or embedded in the surface of the control button. One or more of the control buttons of the first and second set of control buttons 534 and 540 may be illuminated. The illumination of the buttons may also be color coded.

In one configuration, the display 532 is a liquid crystal display (LCD). In another embodiment, the display and one or more of the control buttons may be implemented as a touch-screen display. Nonetheless, other display types may be substituted. The enclosure 520 may also include a warning system in the form of a light.

UI 530 further includes an electronic mode control key switch 550 which is configured to control the mode of operation of MDC device 500. The modes include at least an administration mode and a medication dispensing mode. For example, a caregiver may rotate the key switch 550 to an administration mode when performing administration or supervisory functions such as, without limitation, setup and maintenance. When the key switch 550 is in the dispensing mode, the menus are directed to dispensing operations. In the administration mode, system parameters may be setup or updated by the caregiver.

In one configuration, the key switch 550 is configured to accept a key carried by the caregiver so that the patient or others cannot change the medication dispensing schedule, remove medications or register medications with out administration approval and control. The key switch 550 is one type of security. Another type of security may include, but is not limited to, password entry by the caregiver to permit access to those menus that allow medication information to be changed (e.g., registered, deleted, etc.). The key or password security options may be used alone or in combination. The access key may alternately include an access card reader where a access card with a magnetic strip is slid in the reader.

The first set of the plurality of control buttons 534 may have multiple functions depending on whether the MDC device 500 is in the administration mode or the medication dispensing mode. For example, FIG. 5 illustrates four control buttons in the first set of the plurality of control buttons 534 which, in at least one mode, may be designated as a Y button, N button, a C button and a R button. The second set of the plurality of control buttons 540 provide navigational control with arrow keys. For example, the arrow keys may designate up, down, left and right navigation or movement through menus provided to the patient or the caregiver. A center control button 545 may also be used as an ENTER or SELECT button.

The second compartment 506 provides an enclosure 560 having a primary lid 562 and a secondary dispensing lid 570. The second compartment 506 is hereinafter referred to as the "medication dispensing compartment 506." The primary lid 562 is hingedly coupled via hinge members 564 to a top surface 566 of the enclosure 560. The primary lid 562, when open, provides access to all stored medications or the ability to add one or more new medication containers within enclosure 560. The primary lid 562 is configured to be locked using a key lock switch 568 to prevent unauthorized persons from having access to the patient's medications within enclosure 560. In one configuration, only the caregiver or other system administrators would have a key to open the primary lid 562 so as to control access to and prevent tampering with the patient's medications.

In the exemplary illustration, a mechanical key actuated lock 568 is shown. However, an electronic key pad to enter an access code using an electromechanical locking mechanism may be substituted to control access through the primary lid 562. Nonetheless, other means to control access into a secure enclosure may be substituted. This feature is provided to limit access to the patient and provide full access to the caregiver. A spring loaded momentary interlock switch 780 is provided to provide status information as to whether the primary lid 562 is open or closed. This can be used to prevent operation of the system while the caregiver has the primary lid in the open position.

In the exemplary embodiment, the primary lid 562 includes the secondary dispensing lid 570. The primary lid 562 has formed therein an access opening closed by the secondary dispensing lid 570. The secondary dispensing lid 570 is hingedly coupled via hinge members 572 to the primary lid 562. The secondary dispensing lid 570 may include a knob 574. In operation, when a medication is dispensed by MDC device 500, the secondary dispensing lid 570 may be automatically or manually opened (lifted) so that the user has access to a medication container 600' (FIG. 6) in the medication dispensing position under the secondary dispensing lid 570. The medication dispensing position corresponds to a centered position under the secondary dispensing lid 570, as best seen in FIG. 6. In one configuration, the size of the secondary dispensing lid 570 would permit access to only one medication container at a time.

FIG. 6 is an interior cross-sectional view of the medication dispensing compartment 506 of MDC device 500. FIG. 7A illustrates a top elevational view of the medication dispensing compartment 506 with the primary lid 562 in an open position. The medication dispensing compartment 506 houses therein a medication dispensing carousel 602 rotatably coupled within the medication dispensing compartment 506. The medication dispensing carousel 602 includes a plurality of bins 710A-710J serially-spaced circumferentially around the carousel 602. In the example, ten bins are shown. However, depending on the size of the medication dispensing carousel 602, and the container compartment (bin) size, a greater or lesser number of bins may be provided.

The medication container 600 or 600' may be a standard drug container. Each bin 710A-710J may be loaded with a different medication when the primary lid 562 is in an open position, after the primary lid 562 is unlocked. Since all bins are essentially the same only one such bin will be described in detail.

The top surface 566 is shown with the primary lid 562 lifted. In the exemplary illustration, a locking hole 730 is formed in the top surface 566 to receive a latch (NOT SHOWN) of the key lock switch 568.

Figure 7B:
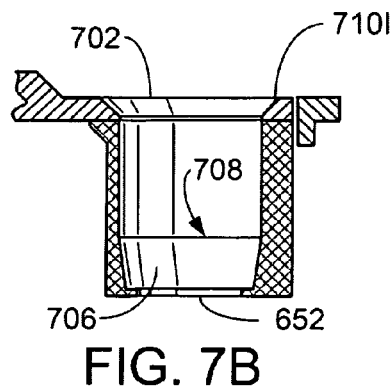
FIG. 7B is a cross-sectional view along the plane 7B-7B of FIG. 7A.

Referring now to FIG. 7B, a cross-sectional view along the plane 7B-7B is shown. Bin 710I is a hollow cylindrically-shaped structure dimensioned to receive and support the medication container (e.g. medication containers 600 or 600'). Bin 710I includes a top open end 702 to receive therethrough a medication container 600 or 600', as best seen in FIG. 6. The top open end 702 is shown with a slight taper. An interior circumferential surface of the bottom end has a slight conical taper 706 to provide a bin seat 708. The taper 706 of the bin seat 708 facilitates the centering of the medication container within bin 710I. The circumference of bin 710I above the bin seat 708 is larger than the circumference of the medication container 600 or 600' so that the medication container 600 or 600' is not in contact with the interior surface of the bin 710I during a weighing cycle (as described in detail below). In FIG. 7B, reference numeral 708 specifically points to a top line of the bin seat 708. The depth of the bin seat 708 may vary. Furthermore, the circumference of the bin 710I may vary. In the bottom of the bin seat 708, bin 710I includes an access hole or opening 652.

Referring again to FIG. 6, when the weighing cycle begins, the stored medication container in the bin seat (e.g., bin seat 708) of bin BD is lifted by a weighing pedestal 623 so that the medication container 600' is not in contact with any surfaces (such as those in the interior of a bin) except the weighing pedestal 623. Bin BD denotes the bin currently being weighed in a weighing position. Bin BD is also the bin in the dispensing position. The weighing position and the dispensing position do not need to correspond to the same position. The medication dispensing carousel 602 is rotated by a shaft 605 extended through a bearing housing 606 containing bearings 607. The shaft 605 extends through base plate 638 within enclosure 560 and is attached to a primary gear 611.

The gear system includes primary gear 611 rotated through contact with a secondary gear 610, wherein the secondary gear 610 is driven by a carousel rotating (stepping) motor 608 through output shaft 609 coupled thereto. Although a single gear reduction is shown more gears can be added to further reduce the speed and increase the torque of the carousel. The gear system provides gear reduction allowing for greater rotational torque and slower rotational speeds than seen at an output of the carousel rotating (stepping) motor 608. The position or location of the medication dispensing carousel 602 with respect to the dispensing position or other predetermined point of reference within the enclosure 560 is monitored or tracked, as the medication dispensing carousel 602 rotates, by a location determining assembly 613. In one configuration, the location determining assembly 613 includes a rotary optical encoder coupled to the driving shaft 605 by a shaft coupler 612.

The positions of all bins (e.g. bins 710A-710J) can be established by rotating the medication dispensing carousel 602 clockwise or counterclockwise through the use of incremental rotational steps delivered by the carousel rotating (stepping) motor 608. In one configuration, a revolution index position detection feature in the optical encoder can be used to establish and align the bin BD storing the medicine (medication container 600') to be dispensed with in the dispensing position under the secondary dispensing lid 570. The bin locations (with respect to the dispensing position) may be determined by either counting stepping motor steps, or by stepping the motor 608 and monitoring the position of shaft 605 via the optical encoder of the location determining assembly 613.

The weighing cycle performed by scale assembly 650 will now be described in detail. The process to weigh a respective one medication container (e.g. medication container 600') includes rotation of the medication dispensing carousel 602 so as to position or align the access hole or opening 652 (corresponding to the bin, or the medication container 600' stored in the bin BD, which is to be dispensed) directly over the weighing pedestal 623. The weighing pedestal 623 has a circumference or diameter which is smaller than the access hole or opening 652 of a corresponding bin. Thus, the weighing pedestal 623 is configured to be lifted through the hole or opening 652 so as to lift the medication container 600' upward and out of the bin seat of bin BD. As a result of said lifting, the medication container 600' is free from contact with the interior surfaces of the bin BD. Accordingly, the (full) weight of the medication container 600' may then rest on the weighing pedestal 623 and transfer a weight force through a lifting column 621 to a load cell (force transducer) 619. An example load cell includes a GS0-250 gram force transducer, manufactured by Transducer Techniques, Inc. The load cell 619 has a maximum weight of 350 grams. Care should be taken to prevent subjecting the load cell 619 to a force (weight) greater then the maximum limit associated with said load cell 619.

A load-cell measuring pedestal 620 receives the load (total force) of not only the medication container 600' but also the weight of the weighing pedestal 623 and the lifting column 621. After measuring said total force, the known weight of the weighing pedestal 623 and the lifting column 621 can be subtracted from said total force to yield a current medication container weight. A linear bearing (NOT SHOWN) is located inside the linear bearing housing 622 to cancel out any lateral force that might be applied to the load cell 619 so as to deliver only a downward force to the load cell 619.

It is important to cancel out any lateral forces on the lifting pedestal. In so doing, the effect of the contents in the container 600' being unevenly distributed within said container 600' should not effect the weighing operation. Teflon is used in one embodiment to create a low cost and low friction sliding surface for the linear actuation of the pedestal 623. Teflon against Teflon has a coefficient of friction of approximately 0.04 and can be easily machined into a linear bearing and lifting column 621. One embodiment of this invention uses a Roberval balance movement (invented by Gilles Personne de Roberval in 1669) which uses a parallelogram movement to direct the load straight down against the weighing pedestal 620, thereby avoiding any side loading or torque on the weighing pedestal. This movement would also cancel any effect from off-center contents in container 600'. This type of movement would also lower the effective friction of the lifting column 621. Of course, numerous other mechanisms for transferring load directly to an electronic load cell may be employed.

Alignment of the weighing pedestal 623 is also important so that when lifted, the pedestal 623 does not hit the bottom of the bin BD around the hole or opening 652. Such a force could be greater then the maximum capacity of the load cell 619 and may damage said load cell. In one configuration, as the weighing pedestal 623 is lifted, such lifting is incremental. Thus, as the medication container 600' is lifted from the bin seat 708, if the force (weight) articulated to the load cell 619 becomes equal to the maximum capacity of the load cell 619, the lifting would be halted and the weighing pedestal lowered (based on preset constants used in the software controlling the microcontrollers 802). The weighing cycle would be aborted and an indication of the overload would be provided through the UI 530 visually and/or verbally.

To raise the weighing pedestal 623 into access hole or opening 652 and raise the medication container 600' for weighing, the load cell 619, load-cell measuring pedestal 620, lifting column 621, linear bearing housing 622, and a weighing frame 616 are raised by lifting the weighing frame 616 using a linear-actuator stepping motor 614. A linear-actuator output shaft 615 pushes on the bottom of the weighing frame 616 and lifts the mentioned components upward. A linear slide assembly 617 is attached to the weighing frame 616 and slides against a vertical rail 618.

During a single weighing cycle, the medication container 600' is weighed N times. The value of N may be 256. The value N may be more or less than 256. While not wishing to be bound by theory, weighing the medication container 600 multiple times reduces the noise experienced by the load cell 619 as the scale assembly 650 performs the weighing function. In the exemplary embodiment, in order to more quickly weigh the medication container 600' (as repeated lifting and lowering could take many seconds), several milliseconds are allowed to pass once the weighing pedestal 623 has been raised so that the container 600' has settled; 256 samples are then taken in succession, approximately one every 12 microseconds, thus the total series of 256 readings are taken in approximately 3072 microseconds (or, one sample per 12 microseconds). The weights (i.e., the 256 readings) taken over the weighing cycle are then averaged, resulting in a single value. The averaging may be calculated locally and/or remotely.

Once the medication container 600' has been weighed, weighing frame 616 is lowered by retraction of the linear-actuator output shaft 615 by the linear-actuator stepping motor 614. Once this is accomplished, medication dispensing carousel 602 can be rotated to locate another medication container 600' for weighing, removal, or identification using RFID tags 640 affixed thereto.

Identification of a medication container occurs when the RFID tag 640 contained on or affixed to the medication container 600 or 600' is located in proximity to the RFID assembly 660. In the exemplary illustration, medication container 600 is in bin BRF, where bin BRF is located in the nearest proximity to the RFID assembly 660. The RFID assembly 660 includes an RFID read/write antenna 624. Although antenna 624 is shown opposite to the scale assembly 650, the antenna 624 can be located anywhere in the full 360 degree rotational arc of the carousel 602. The antenna 624 is supported by an antenna mounting pedestal 625. The antenna 624 is positioned and configured to capture the RFID tag data associated with a RFID tag 640 nearest to the antenna.

The medication container 600 or 600' can be removed from the enclosure 560 by first aligning a respective one of the medication containers 600 or 600' under the secondary dispensing lid 570. The secondary dispensing lid 570 is lifted or rotated about hinge members 572. In the exemplary embodiment, the secondary dispensing lid 570 is automatically opened.

To prevent untimely access to the medication containers 600 or 600', the secondary dispensing lid 570 has a self locking feature which automatically locks the lid 570 to the primary lid 562 to prevent patient access via locking assembly 635 located in or attached to the secondary dispensing lid 570. The locking assembly 635 contains a rotational latch mechanism 629 which rotates about a through pin 631 with the aid of a bearing 632. A solenoid 628 contains an internal return spring which pushes a plunger 637 outward via a linkage arm 633 toward a rotational latch mechanism 629 so as to apply a force to cause rotation about pin 631; thus gripping a latch plate 630 with the lip 640 of the rotational latch mechanism 629. Thus, the secondary dispensing lid 570 is prevented from opening until the solenoid 628 is actuated.

Upon actuation of the solenoid 628 with a control signal (current) from the one or more microcontrollers 802, the plunger 637 pulls the linkage assembly 633 toward the solenoid 628 and causing rotation of the rotational latch mechanism 629 counterclockwise. The rotation lowers the lip 640 of the rotational latch mechanism 629 so as to release the latch plate 630. Releasing the latch plate 630 is an unlocking action allowing the secondary dispensing lid 570 to be opened. Upon closing of the secondary dispensing lid 570 gravity rotates the secondary dispensing lid 570 about the hinge members 572 and forces the latch plate 630 with a beveled edge to push down on the rotational latch mechanism 629 to allow latching. Hence, access to the medication containers in the enclosure 560 by the patient is strictly limited. Access is granted when the secondary dispensing lid 570 is unlocked. In one configuration, the secondary dispensing lid 570 may be automatically open as well.

Figure 8:
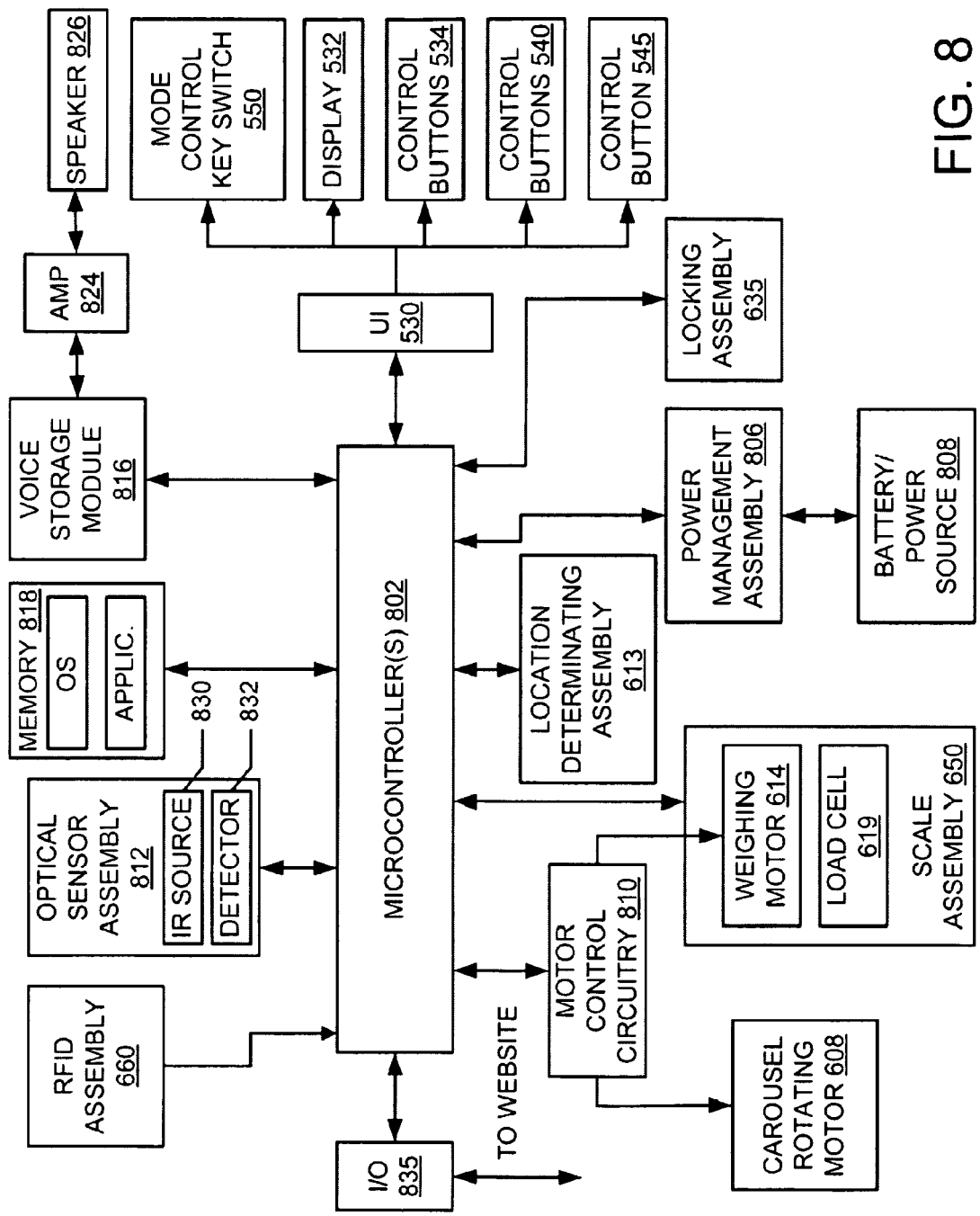
FIG. 8 is a block diagram of the MDC device, in accordance with one embodiment of the present invention.

FIG. 8 is a block diagram of the MDC device 500. MDC device 500 includes one or more microcontrollers 802 serving as the central controller of the MDC device 500. In one embodiment, there are two microcontrollers or separate processing units for performing different functions. In one example, one of the microcontrollers may be responsible for high level functions while at least one other microcontroller handles lower level functions. For example, the microcontroller for high level functions, such as connecting to and communicating remotely through the Internet 1120 (FIG. 11) (where Internet 1120 may be any wide-area computerized network or other similar telecommunications system), may be a RMC4000 RabbitCore® manufactured by Rabbit Semiconductor, Inc. The microcontroller for the lower level functions may be a MC9S08AW32 by Freescale Semiconductor, Inc. Nonetheless, other microprocessors may be used.

The one or more microcontrollers 802 are coupled to a radio frequency identification (RFID) assembly 660, a power management assembly 806, an optical sensor assembly 812, a motor control circuitry 810, a voice storage module 816, a mode control key switch 550, a locking assembly 635 and UI 530.

The one or more microcontrollers 802 detect the state of the mode control key switch 550 to determine the mode of operation of MDC device 500 and to deliver the appropriate menus to display 532. The one or more microcontrollers 802 also control the state (i.e., locked or unlocked) of the locking assembly 635. In response to the dispensing trigger signal and one or more responses for a user, the one or more microcontrollers 802 are configured to send a control signal to unlock the locking assembly 635 which opens the secondary dispensing lid 570.

The power management assembly 806 is also coupled to a battery/power source 808. The battery/power source 808 may be a combination of a battery and/or power from a local utility company or other power source. The battery may serve as a backup power source in the event of a loss of utility power. The power management assembly 806 would detect a loss of power and switch to the battery power source. The power management assembly 806 also controls other power delivery functions.

The motor control circuitry 810 is also coupled to the weighing motor 614 of the scale assembly 650 and the carousel rotating motor 608. When the weighing motor 614 is operational or enabled, the carousel rotating motor 608 is disabled. Likewise, when the carousel rotating motor 608 is operational or enabled, the weighing motor 614 would be disabled. The motor control circuitry 810 is configured to rotate the carousel rotating motor 608 according to a nearest path protocol. Specifically, when a current bin (one in which the medication is to be dispensed) is in a third position clockwise from the dispensing position, the bin is also seven positions counterclockwise from the dispensing position; thus, when the medication associated with the current bin is to be rotated to the dispensing position, the bin is rotated in a clockwise direction corresponding to the nearest path. Similarly, if the next current bin is one position counterclockwise from the dispensing position, the medication dispensing carousel is rotated counterclockwise by one position.

The optical sensor assembly 812 includes an infrared (IR) source 830 and an IR detector 832. While IR is described herein, other wavelengths may be used. The optical sensor assembly 812 is coupled to the primary lid 562 or at some other location in the top of enclosure 560 (said coupling not shown). The optical sensor assembly 812 is configured to determine the presence of the medication container being returned to or removed from a bin seat in the dispensing position.

UI 530 is shown to include display 532, speaker 826 and first and second sets of control buttons 534 and 540. UI 530 is also connected to center control button 545.

The one or more microcontrollers 802 are coupled to memory 818 and voice storage module 816. The memory 818 stores the operating system (OS), application(s) or software, such as those associated with communication via an Ethernet protocol or the like and to perform one or more of the operations of MDC device 500. The voice storage module 816 stores natural voice clips for outputting a voice response or warning to the patient or caregiver through speaker 826. The voice storage module 816 may convert text to speech. The output of the voice storage module 816 is sent to amplifier 824 which amplifies the output and sends the amplified output to speaker 826.

The memory 818 may store information associated with at least the next dispensing cycles for all of the registered medications containers. Thus, in the event of a communication failure between the server and the MDC device 500, the patient's medication may still be dispensed in a timely manner.

Figure 9:
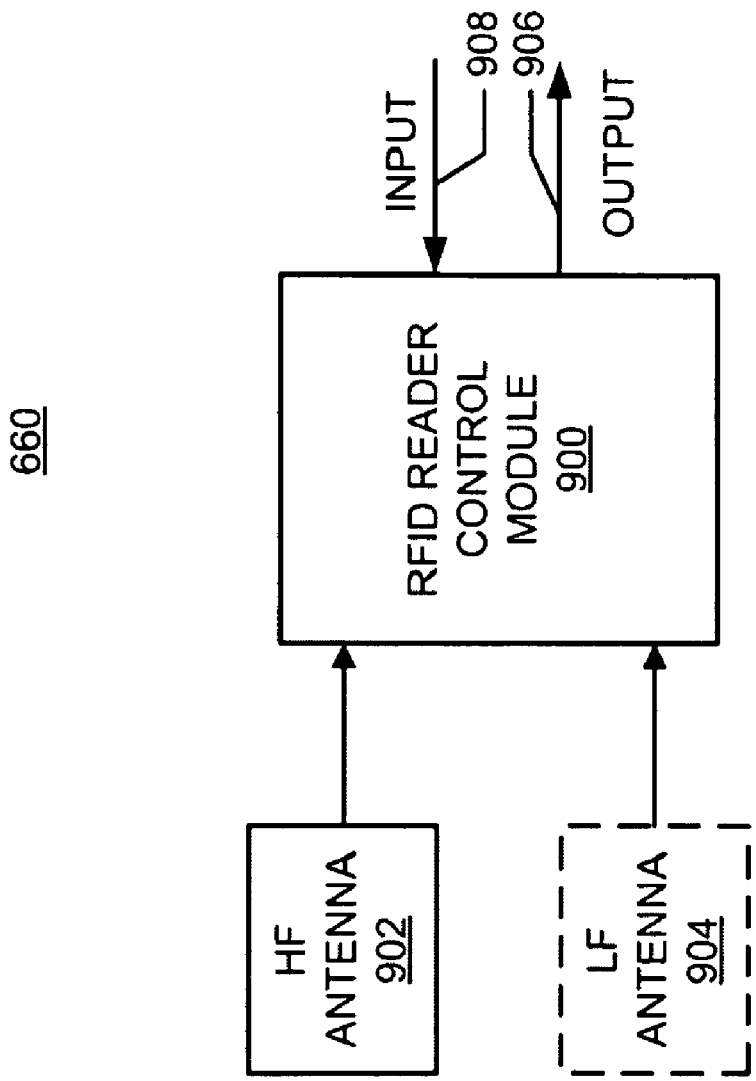
FIG. 9 is a block diagram of a RFID assembly, in accordance with one embodiment of the present invention.

FIG. 9 is a block diagram of a RFID assembly 660. The RFID assembly 660 includes a high frequency (HF) antenna 902 and a low frequency (LF) antenna 904. However, the primary implementation uses the HF antenna 902 as antenna 624. The HF antenna 902 is coupled to an RFID reader control module 900 having a serial output 906 and an input 908. The RFID control module 900 receives power from a power source and is coupled to electrical ground. The RFID assembly 660 may be a TI-S4100HFR/W manufactured by Texas Instruments Inc.

Figure 10:
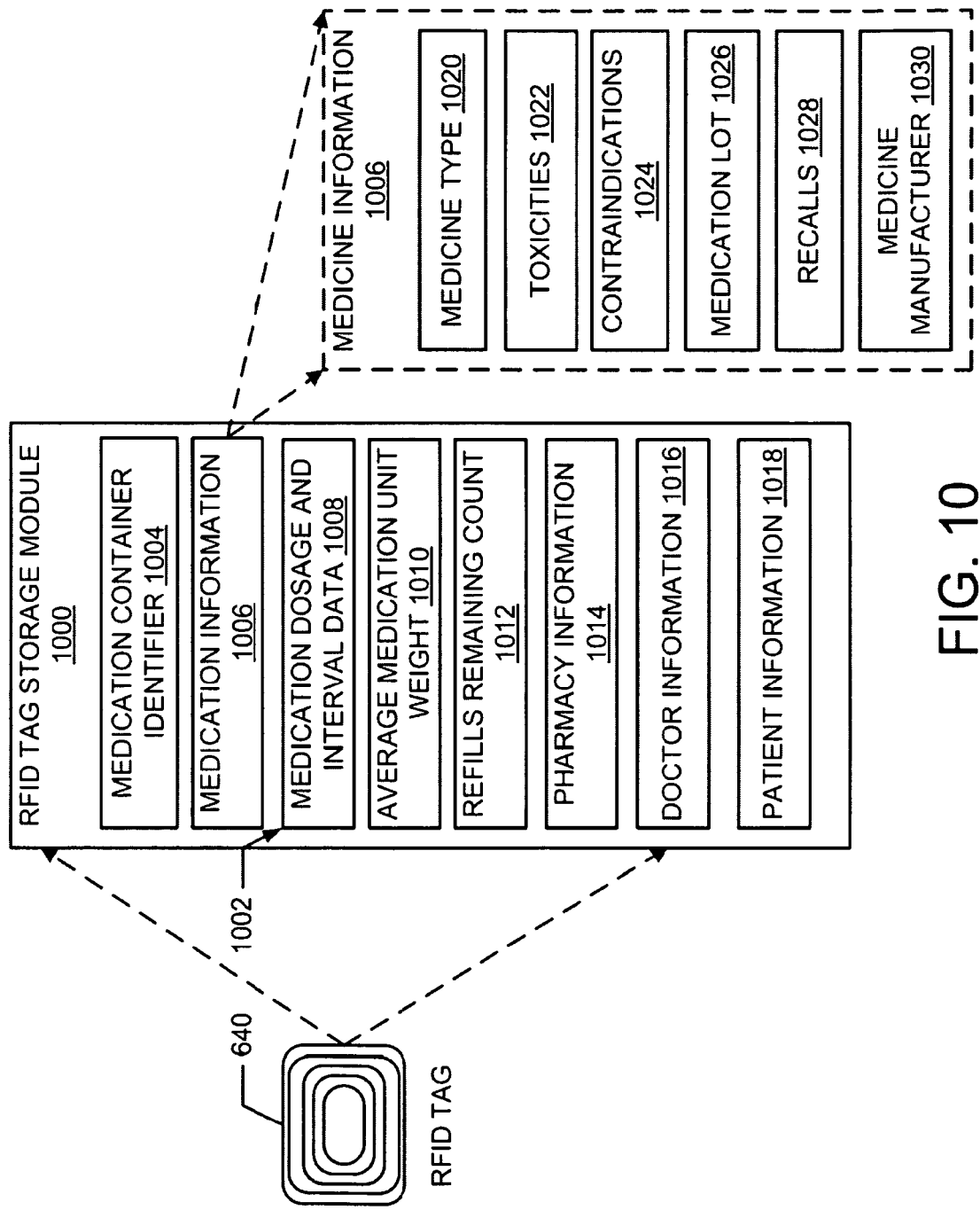
FIG. 10 is a block diagram of an RFID tag storage module of the RFID tag, in accordance with one embodiment of the present invention.

FIG. 10 is a block diagram of an RFID tag storage module 1000 of the RFID tag 640. The RFID tag storage module 1000 includes a plurality of data fields 1002. The plurality of data fields 1002 can include, without limitation, a medication container identifier 1004, medication information 1006, medication dosage and interval data 1008, average medication unit weight 1010, current refills remaining count 1012, pharmacy information 1014, doctor information 1016, and patient information 1018. The medication information 1006 includes fields for medicine type 1020, toxicities 1022, contraindications 1024, medication lot 1026, recalls 1028 and a medicine manufacturer 1030. Other information may be stored in the RFID storage module 1000 based on available capacity and preference of the user.

Figure 11:
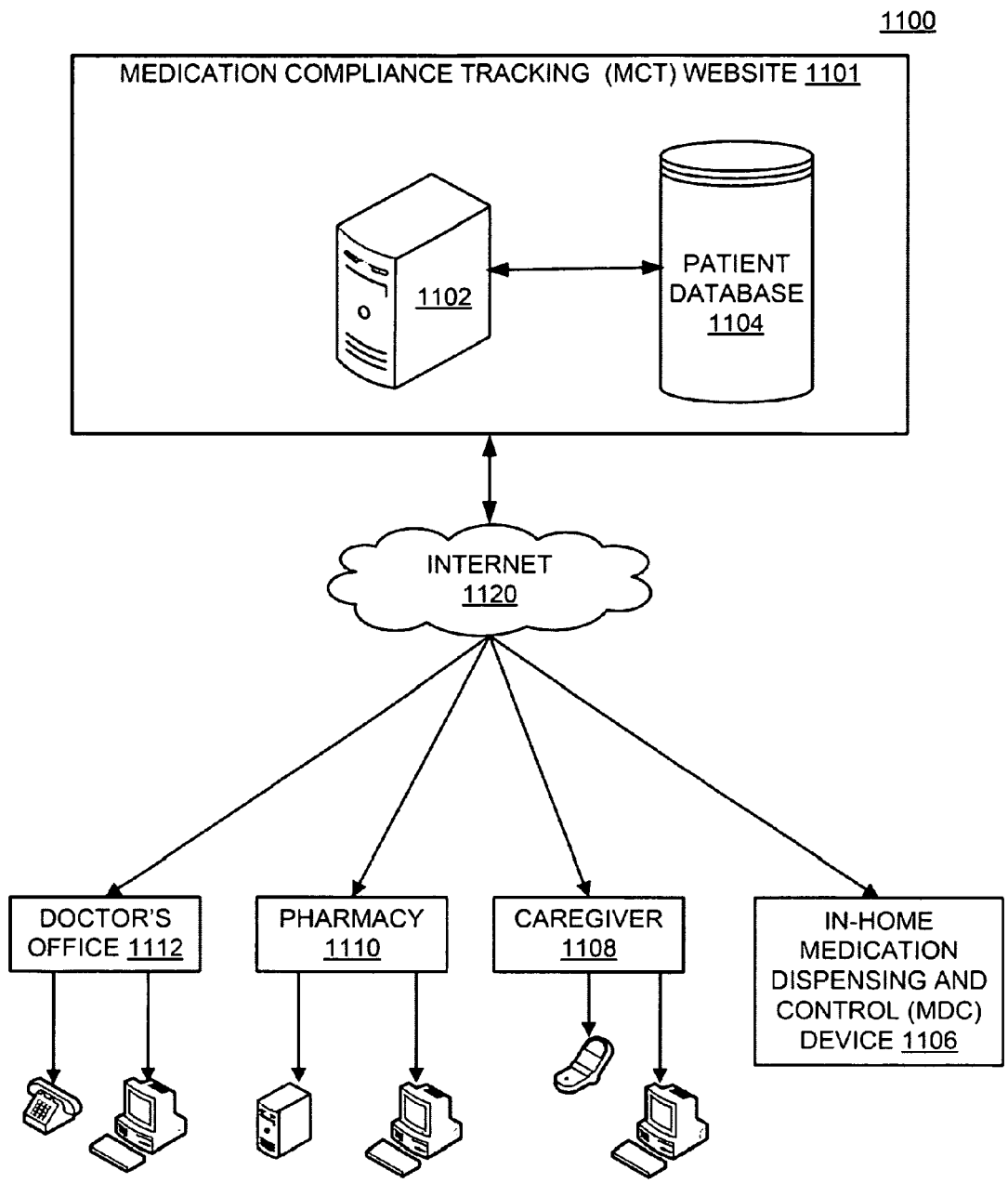
FIG. 11 is a block diagram of a medication compliance tracking (MCT) system, in accordance with one embodiment of the present invention.

FIG. 11 is a block diagram of a medication compliance tracking (MCT) system 1100, in accordance with one embodiment of the present invention. The MCT system 1100 includes a medication compliance tracking (MCT) website 1101 having a MCT server 1102 and patient database 1104. In one configuration, the MCT server 1102 is shown coupled to patient database 1104. The MCT server 1102 is configured to receive signals from the in-home MDC device 1106 representative of all activity associated with the in-home MDC device 1106. The system 1100 further includes an in-home MDC device 1106 configured for wired or wireless communication through the Internet 1120 with the server 1102. The in-home MDC device 1106 may be one of MDC device 100 or 500. The MDC device 1106 is configured to communicate the RFID tag data from the RFID tag storage module 1000 to the server 1102, such as during a medication registration process. Additionally, the MDC device 1106 is configured to communicate one or more weight values of a particular one medication currently dispensed. As previously described, the N-weight values would be transmitted to the MCT server 1102 along with at least one of the medicine container identifiers 1004 (FIG. 10), and the corresponding patient information 1018 (FIG. 10), after the weighing of the medication container so as to associate the current N-weight values with the corresponding medication (container) and patient. In one configuration, the medication container is weighed before and after the dispensing of the medication from the medication container. Thus, the transmission to the MCT server 1102 may include before and after weight values; alternatively, separate transmissions may be sent. The MDC device 1106 is also configured to communicate other information to the MCT server 1102. For example, the MDC device 1106 may communicate to the MCT server 1102 all administration actions taken by the caregiver at the MDC device 1106 such as opening the primary lid 562. The MDC device 1106 may communicate to the MCT server 1102 all responses provided by the patient through the UI 530.

The MCT server 1102 is configured for wired or wireless communication with computers or computing devices of a caregiver 1108, pharmacy 1110 and/or doctor's office 1112. The caregiver 1108 may receive notifications, alerts, emails, pages, automated phone calls, or other communications from the server 1102 through the Internet 1120 via a personal computer (PC), laptop, Notebook, wireless device with Internet access, cellular telephone, landline telephone, personal digital assistant (PDA) device, etc. The caregiver 1108 would also be able to communicate with the MCT server 1102 to cancel or delete prescriptions not necessary, register new patients, provide updated information, or perform other administration functions through graphical user interfaces associated with the website 1101.

The MCT server 1102 may communicate with the pharmacy 1110 through an Intranet or some other server for scheduling a refill. The MCT server 1102 may communicate with the doctor's office through email, telephone calls or other communication medium.

Figure 12:
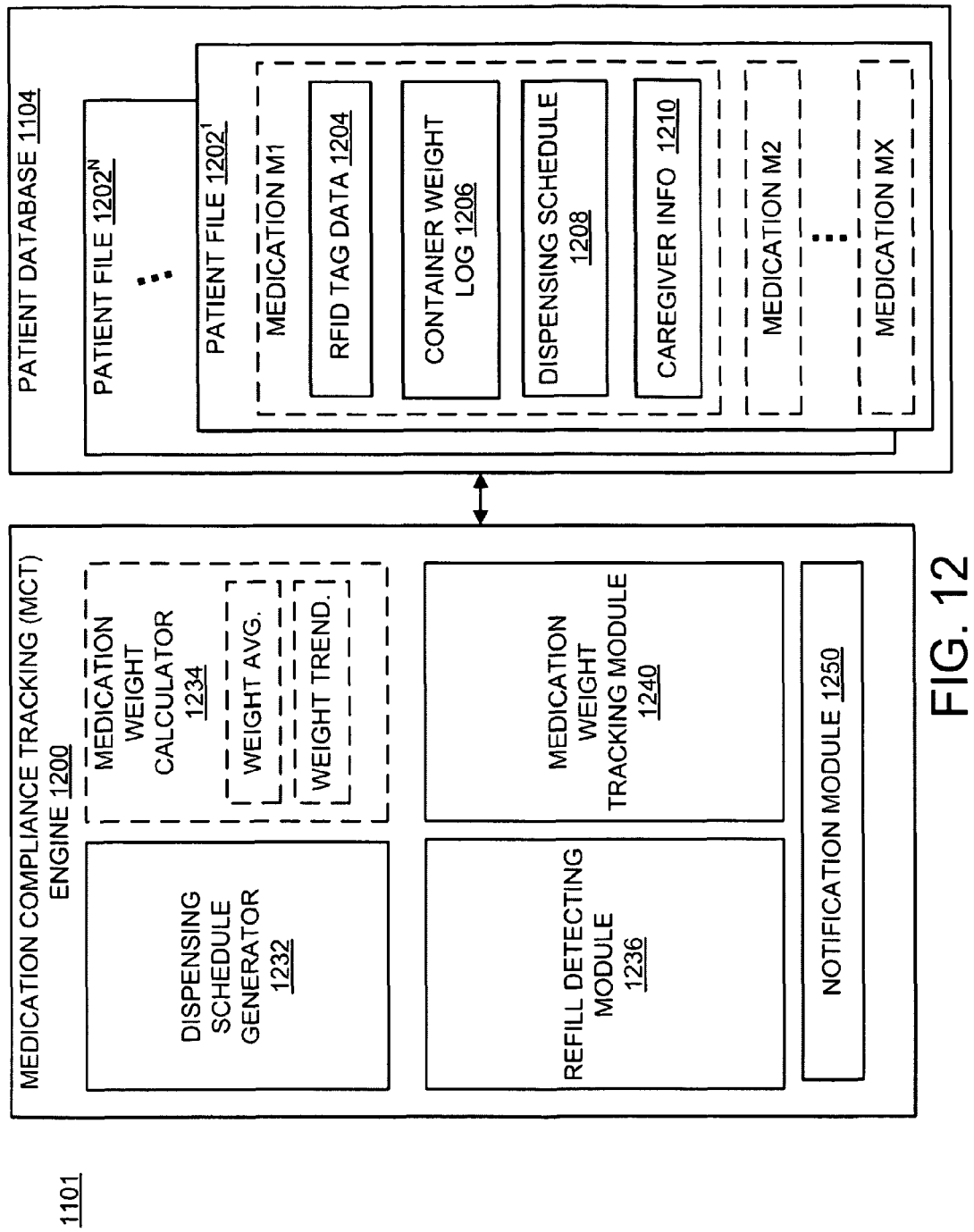
FIG. 12 is a block diagram of a MCT website, in accordance with one embodiment of the present invention.

FIG. 12 is a block diagram of a MCT website 1101. The patient database 1104 includes a plurality of patient files 1202¹-1202ᴺ. Each patient file (e.g., patient file 1202¹) includes one or more medication sub-files M1, M2, . . . , MX. Each medication sub-file (e.g., medication sub-file M1) includes RFID tag data 1204, container weight log 1206, dispensing schedule 1208 and caregiver communication information 1210. Other information may be stored for tracking various features such as the response time of a user during a dispensing cycle.

The MCT website 1101 includes a MCT engine 1200 which includes a dispensing schedule generator 1232, a medication weight calculator 1234, a refill detecting module 1236, a medication weight tracking module 1240 and a notification module 1250. The dispensing schedule generator 1232 determines one or more dispensing times for each medication based on patient file 1202. The refill detecting module 1236 determines when a particular medication needs to be refilled. The refill detecting module 1236 may determine when a refill is scheduled at the time the medication is registered. However, the schedule date may be varied if the medication weight changes. The refill detecting module 1236 would automatically adjust the schedule based on detected variations. For example, some medications are dispensed on an as needed basis. Thus, the refill schedule may be altered (extended or reduced) to accommodate for the "as needed basis" of dispensing. The refill detecting module 1236 produces control signals to the notification module 1250. The notification module 1250 produces a plurality of alerts or notifications as described below in relation to Table 1.

The medication weight calculator 1234 calculates the weight based on a weight average algorithm or a weight trend algorithm. The weight average algorithm calculates the weight of the medication based on the N-weight values of the medication container. In one configuration, the medication container is weighed consecutively 256 (N=256) times. Nonetheless, N may be more or less than 256. The weight calculator 1234 takes an average of the N-weight values to derive the average dispensed weight. The calculated average dispensed weight is entered into the container weight log 1206.

The medication weight calculator 1234 is shown in a dashed box to denote that the calculator 1234 may alternately be placed in the MDC device 1106. Thus, the MDC device 1106 would calculate the average dispensed weight and send one weight value to the server.

The medication weight tracking module 1240 will track during a particular dispensing cycle whether an under-dosage, over-dosage, or non-compliant dosage has occurred. In other words, the medication weight tracking module identifies a compliant state, an under dosage state, an over dosage state or other non-compliant state. Based on the identified state a control signal may be sent to the notification module 1250 to generate the necessary alerts.

Some medications have a miniscule weight. Thus, the detection of changes in weight can create some challenges. In these situations, one configuration of the present invention would use a weight trend algorithm, as opposed to an averaging algorithm, to detect a weight decline over time.

It is contemplated that each patient would likely have one or more medications, thus a medication sub-file M1, M2, . . . , MX for each medication is generated as each said medication is registered. Thus, each sub-file serves to track and log the dispensation of the medication in each medication container 600 independently.

The caregiver 1108 provides the communication mode(s) to provide emails, alerts, notification, telephone calls, etc. For example, if a refill has not been detected, both the pharmacy and caregiver may be notified with a Refill notification generated and sent by the notification module 1250. The alert to the pharmacy initiates the refilling of the medication while the alert to the caregiver may be a notification of submission of the refill order. However, if a new medication container 600 of the same prescription has not been substituted prior to expiration of the medication, then the caregiver 1108 will be alerted by the notification module 1250. Further, if the contents of the medication container 600 have been expended without a refill detected, a higher priority Out-of-Medication alert or notification would be generated and sent to the caregiver 1108 by the notification module 1250. A list of exemplary alerts and notifications produced by the notification module 1250 is shown in Table 1.

TABLE 1

| Notification | Recipient | Trigger |
| --- | --- | --- |
| Missed Dosage | Patient, Caregiver | Expiration of a Dispensing Cycle Timeout |
| Non-compliant Dosage | Caregiver | Current weight not within range of expected weight |
| Over Dosage | Patient, Caregiver, Doctor | Current weight not within range of expected weight |
| Unreturned Medication Container | Patient, Caregiver | Detection of unreturned Medication Container |
| Refill | Caregiver, Pharmacy | Based on weight or refill schedule |
| Out-of-Medication | Caregiver, Patient | Non-detection of Replacement Medication Container |
| Out-of-Refills | Doctor, Caregiver, Patient | Detection of the refills remaining count = 0 |
| Fault Detection | Caregiver | Any failure condition |

The caregiver 1108 may be alerted or notified of any medication dosages missed by the patient. The MCT engine 1101 is part of server 1102 and is configured to send a signal through the Internet 1120 to the MDC device 1106 to cause the MDC device 1106 to alert the patient when a medication is ready for dispensing. However, if the medication is not dispensed or taken after a predetermined timeout interval, the caregiver 1108 is alerted of a Missed Dosage by the notification module 1250. Prior to the timeout interval, the patient is given numerous verbal and/or visual alerts or warnings. The timeout interval may be the same for all medications or may be varied based on the criticality of the medication to the patient's health. The caregiver 1108 may be notified immediately if a medication, after being dispensed, has a weight (average or trend) which is less than a predetermined threshold such as may be the result of an overdose or theft. In such an event other triggers may be included such as to adjust the dispensing schedule or refill schedule, as necessary.

The MCT engine 1200 would dynamically adjust the next scheduled dosage as necessary based on toxicities and contraindications stored for the medication when an over-dosage condition is detected. The schedule may be resumed based on an administration override. It is observed that an over-dosage condition does not mean that the patient actually overdosed. Instead, someone may have stolen some of the medication or some medication may have been spilled or accidentally lost. Thus, the MCT engine 1200 can dynamically adjust the schedule and medication sub-file for such conditions.

The MCT engine 1200 may also dynamically adjust the schedule and medication sub-file for medications taken on an as needed basis. For example, using the R button of the first set of control buttons 534 may serve as a means for a patient to request a medication registered as an "as needed basis" medication. Furthermore, medications that are dispensed on an "as needed basis" may also be dispensed on a schedule; however, in this circumstance, missing a dosage would not necessarily automatically generate an alert or notification due to the optional nature of the medication at issue.

Figure 13:
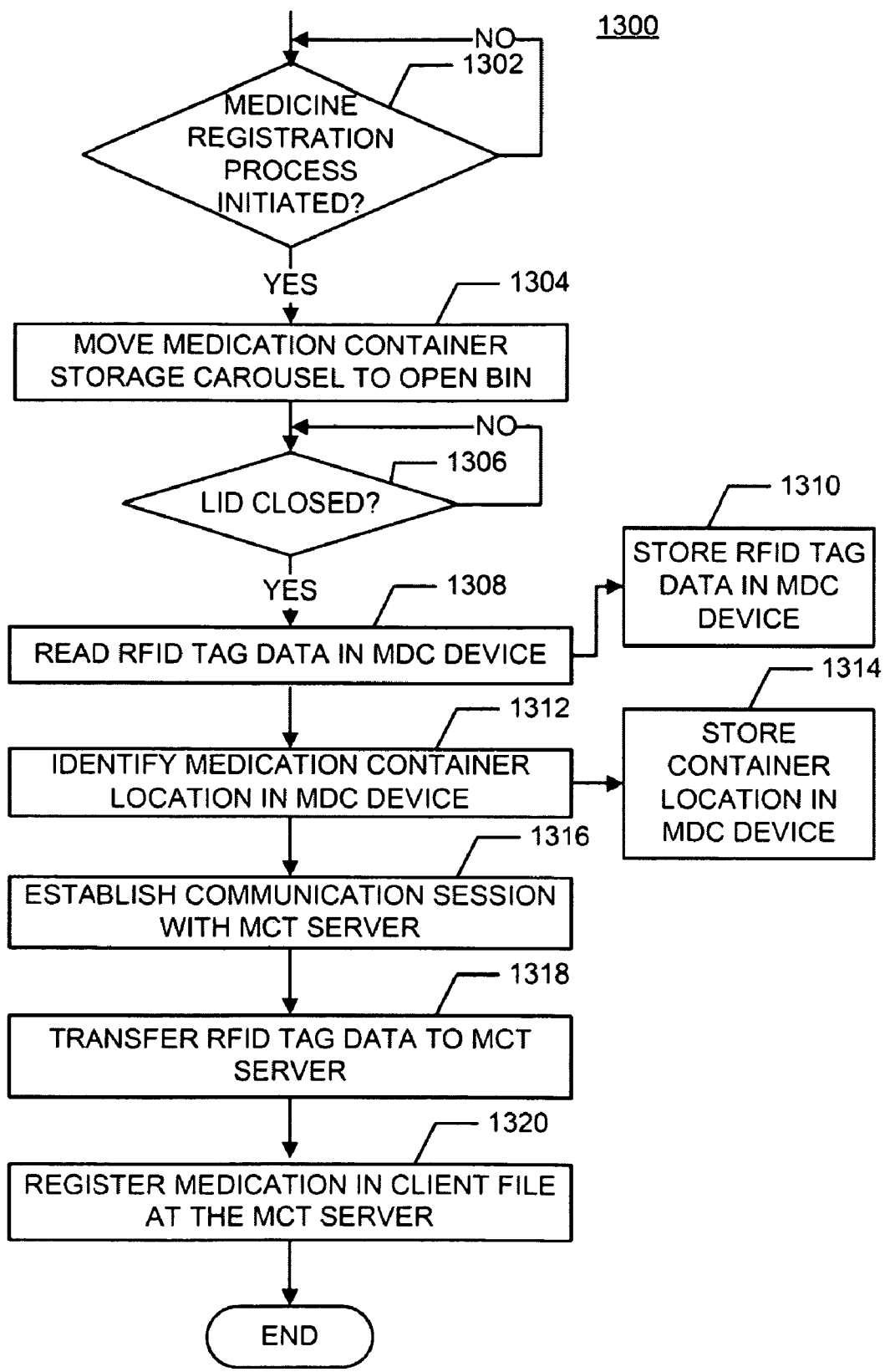
FIG. 13 is a flowchart of a medicine registration process, in accordance with one embodiment of the present invention.

FIG. 13 is a flowchart of a medicine registration process 1300. In various configurations, the blocks of the process 1300 and other processes described herein are performed in the depicted order or at least two of these steps or portions thereof may be performed contemporaneously, in parallel, or in a different order. Furthermore, one or more of the blocks may be omitted.

The medication registration process 1300 includes determining that a medication registration process is initiated such as by a caregiver 1108 at the MDC device 1106. For example, the caregiver 1108 would cause the MDC device 1106 to be configured into the administration mode. The caregiver 1108 would select the registration mode at block 1302. For example, the R control button may be used to indicate registration mode when in an administration mode. A menu displayed on the display 532 would provide instructions to register the medication/medication container. At block 1304, the carousel 602 is automatically rotated to place an empty bin in the dispensing position. The secondary access lid 570 may then be permitted to be opened. At block 1306, a determination is made as to whether the lid is closed. If the determination is NO, the process 1300 waits. When it is determined that the lid is closed at block 1306, the MDC device 1106 is configured to automatically rotate the newly entered medication container 600 so as to position its location for reading of its RFID tag 640 at block 1308 and store the RFID tag data at block 1310 in the MDC device 1106. The storage of the RFID tag data may be placed in memory 818 temporarily or permanently. At block 1312, the MDC device 1106 identifies the medication container location or bin and stores the location at the MDC device at block 1314. At block 1316, the MDC device 1106 establishes a communication session with the MCT server 1102. At block 1318, the MDC device 1106 transfers the RFID tag data to the MCT server 1102. At block 1320, the MCT server 1102 registers the medication/medication container in a corresponding patient file and verifies the acceptance of this medication container based on prior data located in patient data base 1104.

A secondary method of medication container registration would be for the caregiver 1108 to manually open the primary lid 562, place a medication container or containers 600 into any vacant bin 710A through 710J. The primary lid 562 could then be closed and the R control button initiated. A selection using switches 540 and 545 and screen 532 could set up a group registration process to register all the new medication containers automatically. In the group registration process, the blocks of process 1300 would be modified such that block 1304 would be omitted. Then blocks 1308 and 1312 could be repeated for each new medication container. This automatic registry would require the MDC device 1106 to rotate a full 360 degrees reading each RFID tag 640 and collecting all RFID tag information. After this operation is completed, the MDC device 1106 could determine the identity of new drugs entered into the system and communicate this information back to the MCT server 1102 for storage in the patient data base 1104.

Figure 14:
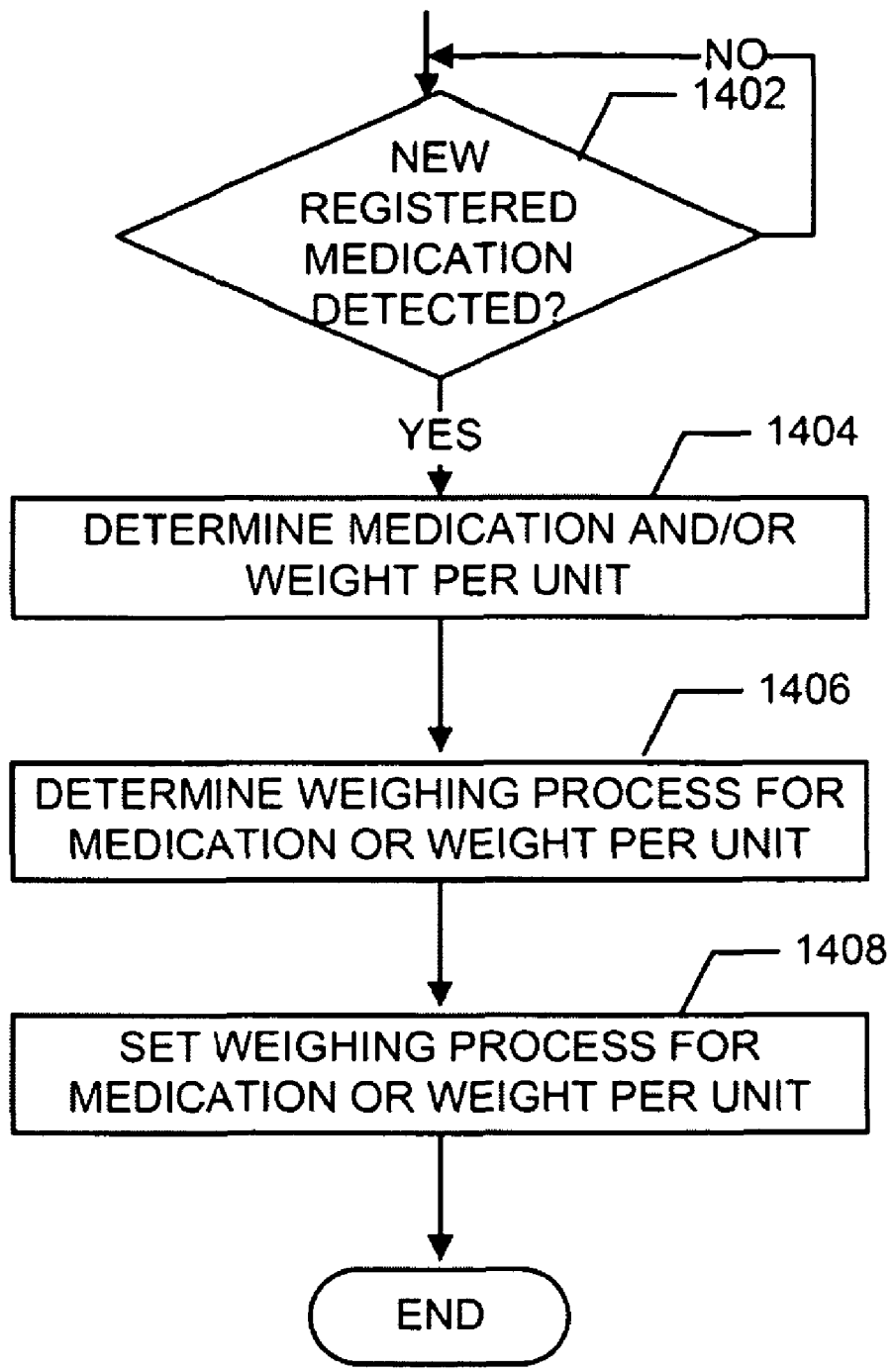
FIG. 14 is a flowchart of a weighing setup process, in accordance with one embodiment of the present invention.

FIG. 14 is a flowchart of a weighing setup process 1400. The weighing setup process 1400 includes determining that a new medication registration has taken place at block 1402. If the determination is NO, the process 1400 waits for a new medication registration to occur. If the determination is YES, then at block 1404, the medication and/or weight per unit is determined. At block 1406, a weighing process is determined for the mediation and/or weight per unit. The weighing process is selected from at least one of a weight average algorithm or a weight trend algorithm; nonetheless, other weighing processes may be used. For example, instead of calculating an average, a single weight may be taken. At block 1408, the weighing process is set for the currently registered medication.

Figure 15A:
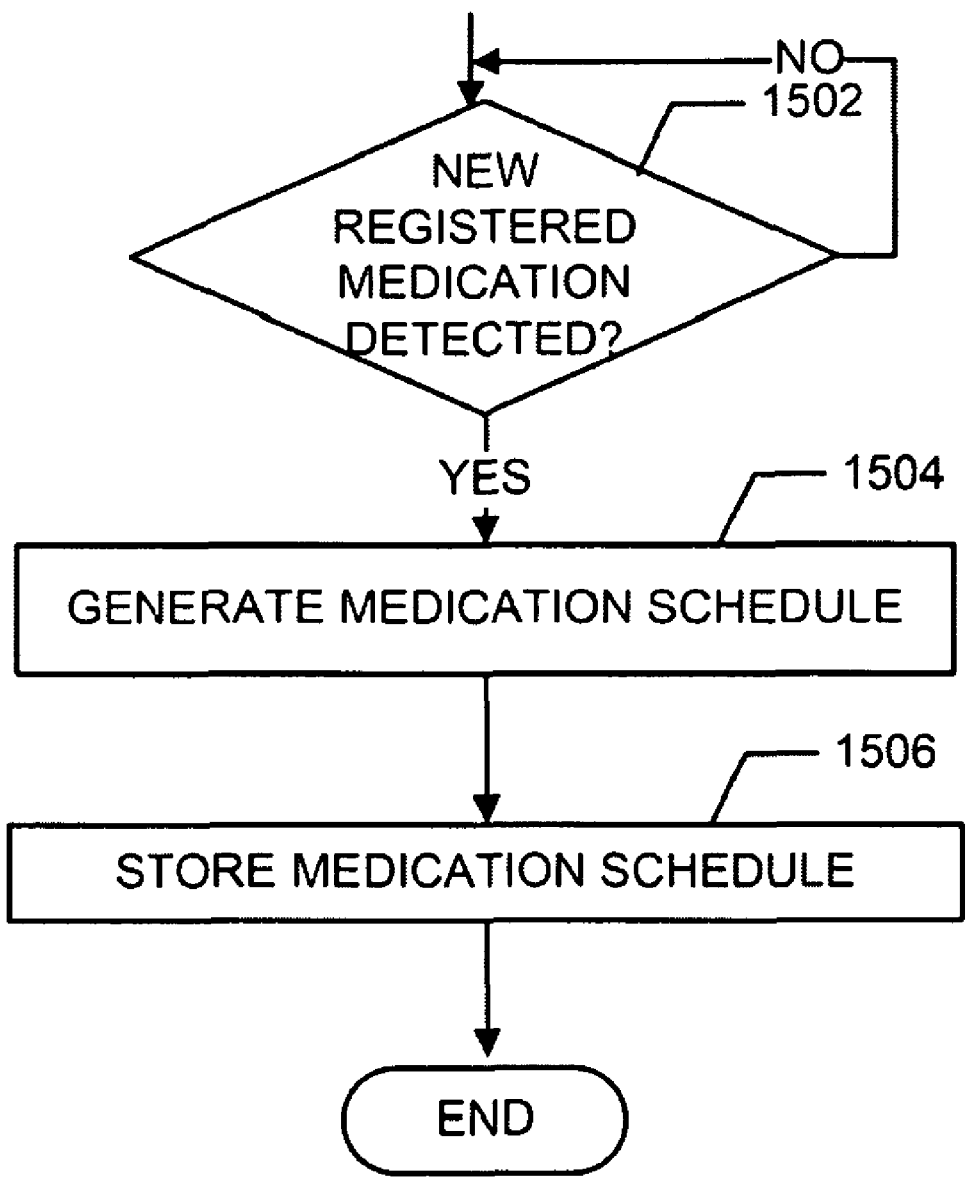
FIG. 15A is a flowchart of a medication schedule setup process, in accordance with one embodiment of the present invention.

FIG. 15A is a flowchart of a medication schedule setup process 1500, in accordance with one embodiment of the present invention. The medication schedule setup process 1500 begins at block 1502 where determination is made whether a new medication registration has taken place at block 1502. If the determination is NO, the process 1500 waits for a new medication registration to occur. If the determination is YES, then at block 1504, a dispensing schedule for the medication is generated. The dispensing schedule may be based on the medication dosage data and interval data 1108 or one or more scheduled times for other medications associated with the same patient or a combination. The dispensing schedule may be based on one or more of recommendations, toxicities and contraindications. For example, some medications are best taken at night if the medication may cause drowsiness, while others may need to be taken before meal time. At block 1506, the dispensing schedule for the mediation is stored in the dispensing schedule 1208 associated with the medication.

Figure 15B:
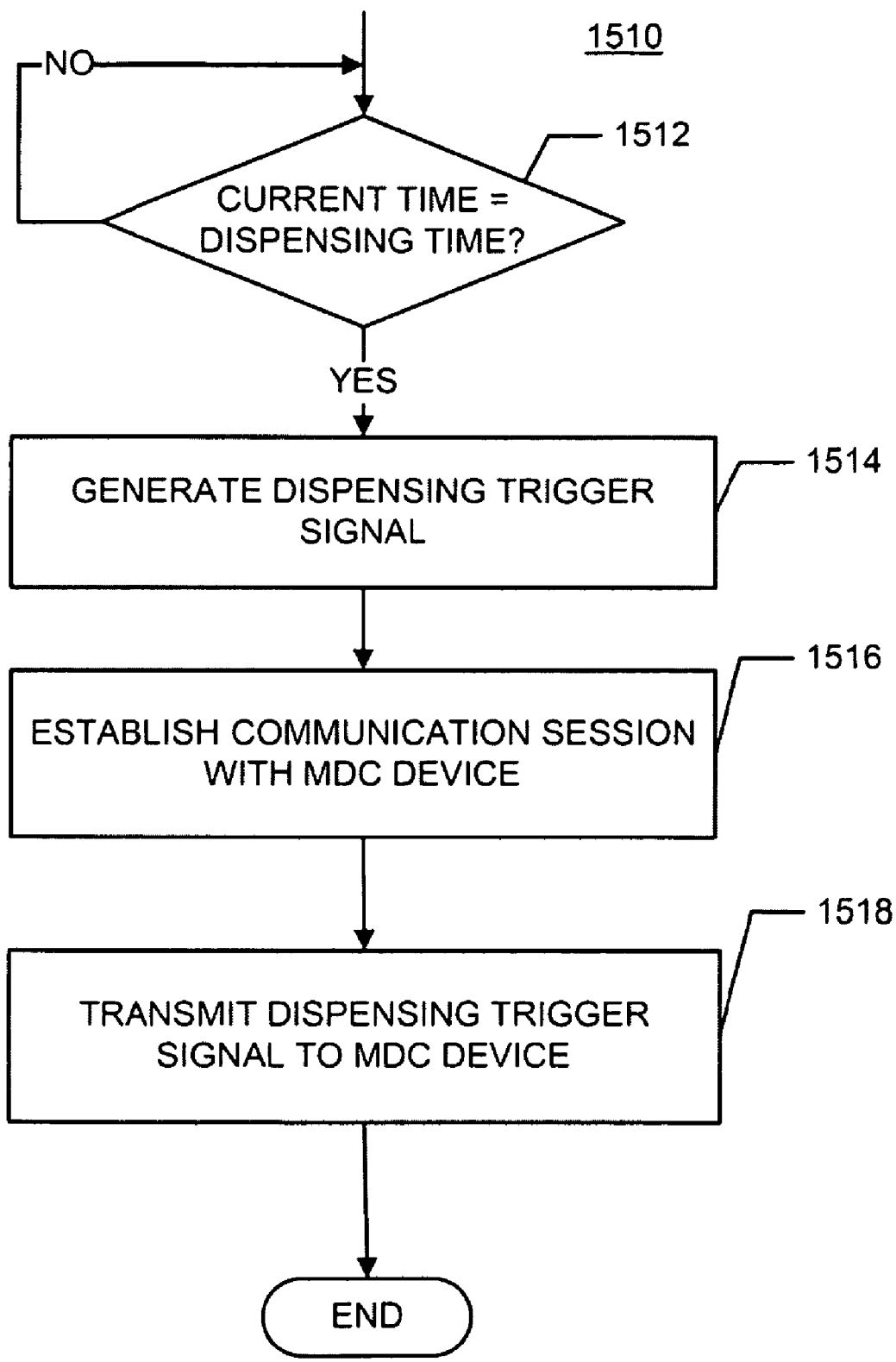
FIG. 15B is a flowchart of a medication dispensing triggering process, in accordance with one embodiment of the present invention.

FIG. 15B is a flowchart of a medication dispensing triggering process 1510. At block 1512, a determination is made whether a current time is equal to the dispensing time from the dispensing schedule 1208. If the determination is NO, the process 1510 waits. However, if the determination is YES, the process 1510 proceeds to block 1514 where a dispensing trigger signal is generated by the MCT server 1102. At block 1516, a communication session is established between the MCT server 1102 through the Internet 1120 to the MDC device 1106. At block 1518, the MCT server 1102 is configured to send the dispensing trigger signal to the MDC device 1106.

Figure 16A:
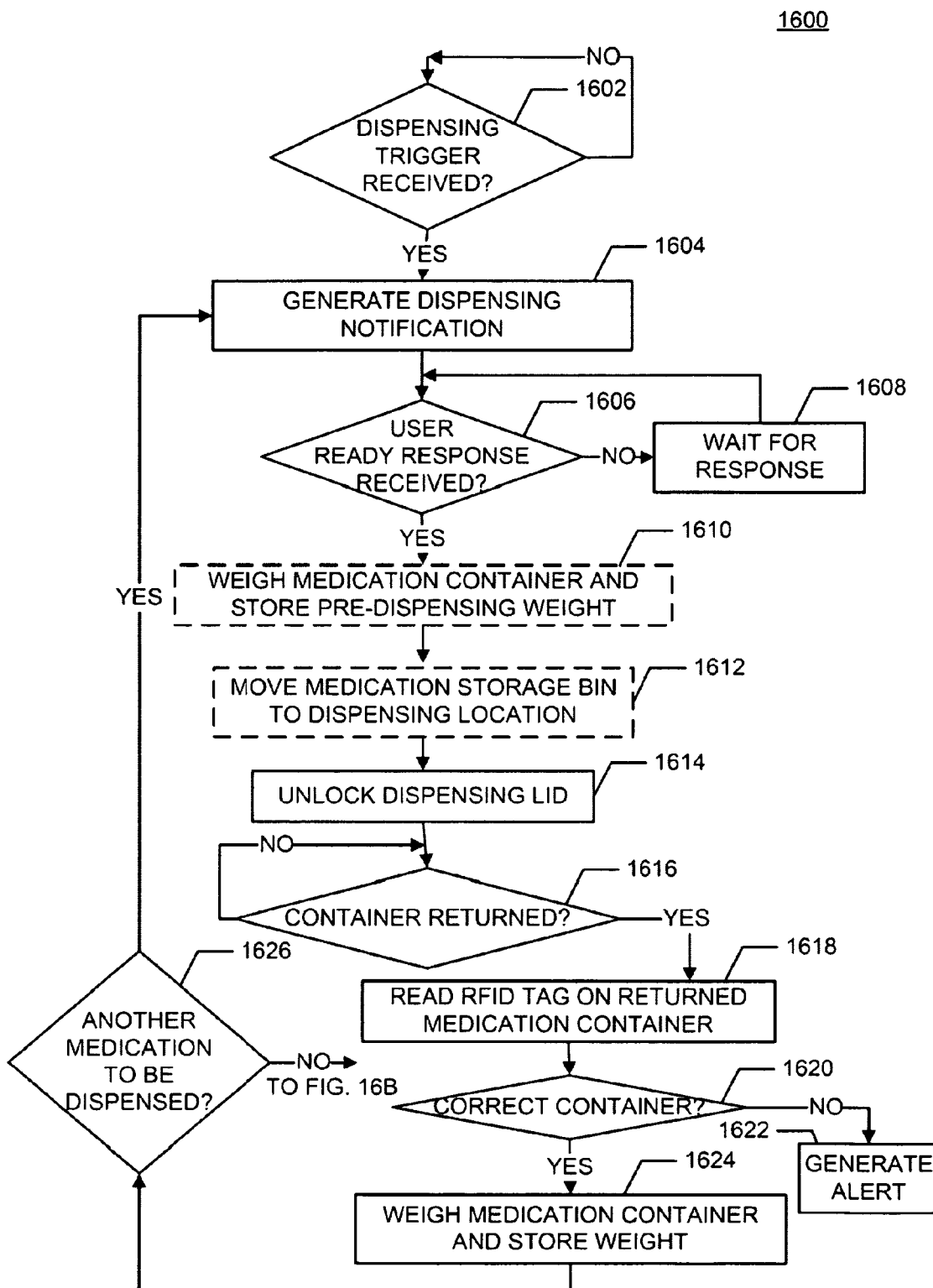
FIGS. 16A and 16B are a flowchart of a medication dispensing process, in accordance with one embodiment of the present invention.
Figure 16B:
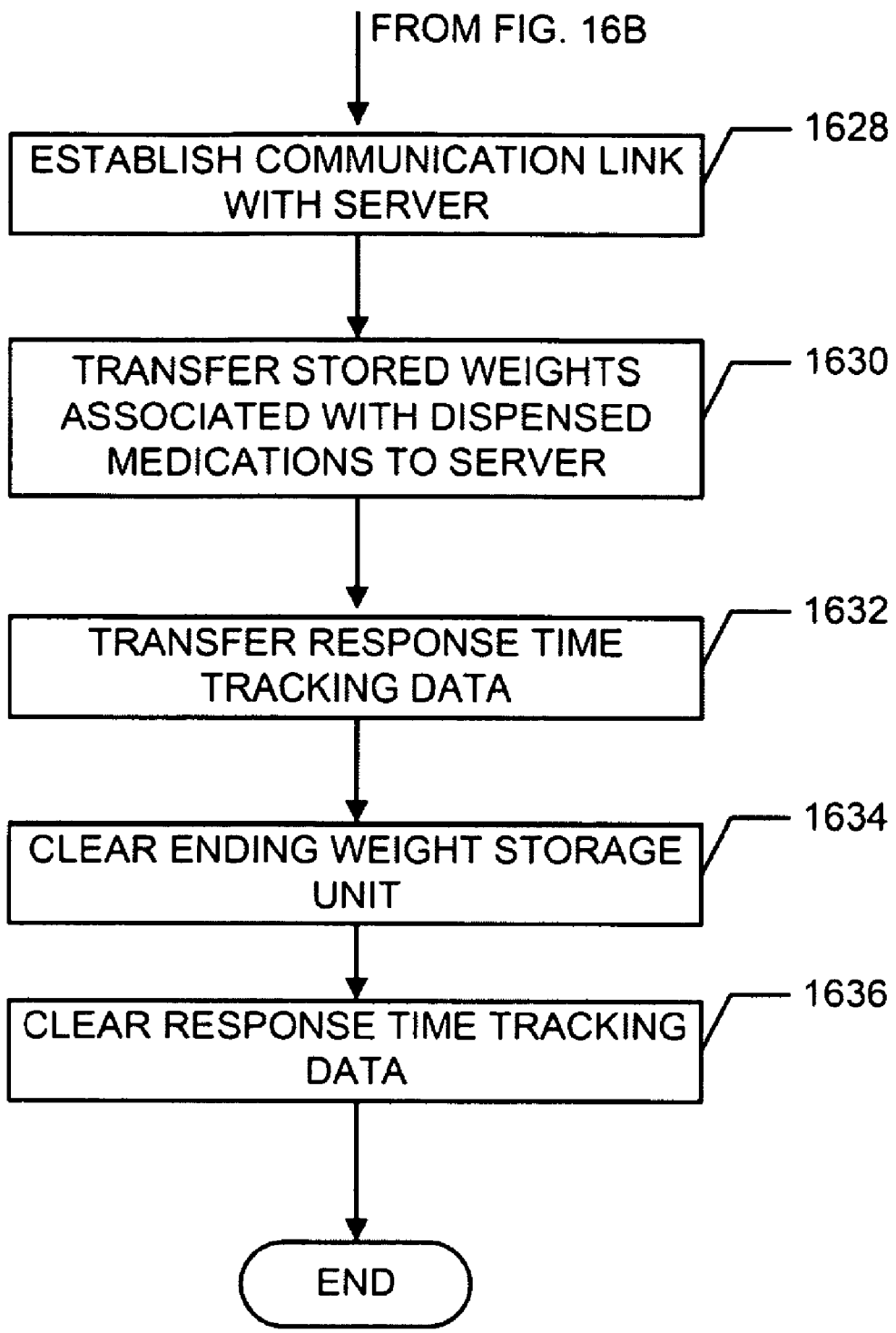

FIGS. 16A and 16B are a flowchart of a medication dispensing process 1600. The medication dispensing process 1600 includes determining whether a dispensing trigger signal has been received at the MDC device 1106 at block 1602. If the determination is NO, the process 1600 waits. If at block 1602 the determination is YES, the process 1600 generates a dispensing notification to the patient at block 1604. The dispensing notification to the patient would produce an audible output through speaker 826, a visual display using display 532 or a combination of both audible and visual notification sequences. In one configuration, questions that would be asked of the patient, instructions or any other prompt would be given to the patient to determine whether the patient is ready for the medication to be dispensed. For example, the MDC device 1106 could ask a question either in text or verbally to determine a patient's readiness to take their medications. Moreover, one or more of the control buttons could be illuminated to enter a response. The questions may require an immediate response from the patient.

At block 1606 a determination is made whether the user has entered a ready response. If the determination is NO, at block 1608, the response is waited for. Block 1608 loops back to block 1606. If the determination is YES, then at block 1610, the medication container is weighed to determine a pre-dispensing weight by the scale assembly 650. To weigh the medication container, the carousel 602 may need to be rotated to the scale assembly's location. The pre-dispensing weight is stored. At block 1612, the bin with the medication to be dispensed is moved to the dispensing position, if necessary. In the exemplary configuration, the scale assembly 650 and the dispensing position are in the same location (thus block 1612 is not necessary for the exemplary configuration). However, if the scale assembly 650 is positioned anywhere other than the dispensing position, so as to weigh a medication container in a bin location other than the dispensing position, then block 1612 should be executed.

At block 1614, the secondary dispensing lid 570 is unlocked. At block 1616, a determination is made whether the container has been returned to the bin. If the determination is NO, the process 1600 waits. In the exemplary embodiment, a timeout is set so as to generate an alert that the dosage has not been taken. If the determination is YES, then at block 1618, the RFID tag 640 is read on the returned medication container 600 to verify that there is a match with the dispensed medication container 600. If the correct container is not detected at block 1620, one or more alerts/notifications are generated at block 1622 and sent appropriately to the website 1101. If at block 1620, the correct container was determined to be returned, the medication container is weighed and the weight is stored at block 1624. At block 1626, a determination is made whether another medication is to be dispensed. If the determination is YES, the process 1600 returns to block 1604 to notify the patient of another medication that is ready for dispensing. However, if the determination at block 1626 is NO, block 1626 is followed by block 1628 of FIG. 16B. It should be noted, that block 1618 may also be performed prior to unlocking the dispensing lid at block 1614 as a self-checking operation or to ensure that the proper medication is being dispensed from the correct bin. For example, after any one particular medication container is registered, if the primary lid is opened, all medication container locations may require synchronization before dispensing the next medication from any one medication container.

At block 1628, the MDC device 1106 establishes a communication session with the MCT server 1102. At block 1630, the stored weights associated with the dispensed medication are transmitted to the MCT server 1102. The process 1600 may also track the response time of the patient using the MDC device 1106, thus, the response time or information indicative of a response time could be sent to the MCT server at block 1632. At blocks 1634 and 1636, the weights and the response time tracking data, respectively, may be cleared from the memory or registers of the MDC device 1106.

Returning to block 1606, the response entered by the user may be accomplished by the control buttons denoted as Y and N in FIG. 8. The questions to the patient may be phrased so as to illicit either a "Yes" or "No" as an answer. Thus, the control buttons denoted as Y and N provide a Yes or No response, respectively, if selected. These control buttons would be in an illuminated state while the other control buttons would be in a non-illuminated state. Once the patient replies, such as by selecting one of the illuminated control buttons denoted as Y or N, the one or more microcontrollers 802 are configured to navigate to the next set of instructions in the dispensing sequence. If any control buttons selected that are in a non-illuminated state or not part of the selection set provided to the patient, the MDC device is configured to generate a notification audibly or visually that the response was an incorrect response.

If at anytime during the interaction with the MDC device 1106 the patient gets confused, one of the control buttons would allow the patient to restart the dialog or to navigate to a previous sequence set awaiting a response from the patient. For example, control button denoted as R could be used in the case where a patient became confused over where they were in the machine-patient information interchange. The control button denoted as R would initiate software controlled actions to return the patient to a familiar starting location in the logic of the interchange thus allowing the patient to become reoriented, possibly from a point more progressed than the starting location, but prior to the point where the patient become confused.

Control button denoted as C may be used to cancel an action or clear an action to allow for a change in mind by the patient as the information was entered. Repeated activation of control button denoted as C could result in bringing the patient back to the beginning of the exchange.

Prescription Medication Control Method

Preferably, the prescription medication control system apparatus is used at the home of a person, though it could be beneficial in commercial environments such as pharmacies as well. The user introduces a prescribed medication to the MDC device 100 in FIG. 1 by first placing the medication container 120 in an empty receptacle well 130 in FIGS. 1, 2, and 3 or MDC device 500. Preferably, the medication containers 120, 600 or 600' are standard-sized pharmaceutical bottles, but a stepped narrowing of the housing 130 could accommodate medication containers 120 of different sizes. After the medication containers 120, 600 or 600' enter their respective receptacle wells 130 or bin, information associated with the particular medicines is identified by the MDC device 100 or 500. The data gathering can be accomplished using a plurality of technologies. Preferably, RFID tags 640 would be used to determine what type of medication is contained in the medication container 120, 600 or 600', how much the average pill or unit of the particular medication weighs, and which receptacle well 130 in FIGS. 2 and 3 houses the particular medication container 120, 600, 600' in FIG. 1. Additional information concerning the pharmacy, physician, family members' contact information, toxicities, contraindications, number of times the particular medication has been renewed, date of prescription expiration, medication lot, recalls, and manufacturer (by, for instance, a 3-4 letter code associated with each manufacturer) could also be embedded in a RFID tag 640 associated with the medication container 120, 600 or 600'. The RFID information could also be obtained via other means such bar codes or manual entry, though RFID technology would be the least cumbersome.

After a medication container 120, 600 or 600' is inserted into a receptacle well 130 or bin, the container 120, 600 or 600' is centered in the well 130 or bin via a tapered bottom of said bin 130. When it is time for a user to take a particular medicine, the MDC device 100 or 500 moves the load cell 200 or 619 and pedestal 190 or 623 to a position directly below the particular receptacle well or bin 130 that houses the needed medication container 120, 600 or 600'.

The lock-out cam 290 is activated and pushes the plunger 170 into the bottom of the retainer 140. This removes the top of the retainer 140 from the top of the needed medication container 120, which also unlocks the container 120. The load cell 200 and pedestal 190 are then raised to support the weight of the medication container 120. At this point, the medication container 120 is weighed by the load cell 200. The user then lifts the medication container 120 out of the receptacle well 130 and removes the appropriate dosage of medication. The user replaces the medication container 120 into its respective receptacle well 130, and the load cell weighs the medication container 120 a second time.

The MDC device 100 or engine 1200 may determine a missing amount of medication. For example, the missing amount of medication is calculated by determining a difference between the initial weight and the second weight. The difference is then divided by the average weight of a single pill, medication or unit of the particular medication that was stored when the particular medication container 120, 600 or 600' was registered in the MDC device 100 or 500. The missing amount calculation determines the number of pills missing from the medication container 120, 600 or 600' and avoids the problem of trying to evaluate the absolute number of pills or units in each container 120, 600 or 600'. This problem stems from the certain amount of error in each pill or unit's mass. Cumulative errors may lead to a severe miscalculation of dosage for the user. Preferably, each medication container 120, 600 or 600' is weighed before every removal and after every replacement. However, the medication container 120, 600 or 600' could only be weighed after every removal if the MDC device 100 or 500 stores that weight each time in order to compare it with the next removal in its calculations.

In the embodiment of FIGS. 1-4, after a medication container 120 is replaced in its receptacle well 130, the load cell 200 and pedestal 190 are lowered, and the retainer 140 returns to a locked position over top of the medication container 120. The MDC device 100 maintains this state until it is time for the user to take another dosage of a medication housed in the MDC device 100. This lock-out feature helps prevent a user from taking a medication more times than required or allowed in one day or any other time period. The MDC device 500 includes a similar lock-out feature.

Additionally, the MDC device 100 or 500 is able to communicate with a remote location such as a physician or family member. The MDC device 100 or 500 uses the Internet 1120, a landline telephone, or a mobile phone for communication with a third party by means of TCP/IP (Transmission Control Protocol/Internet Protocol), UDP (User Datagram Protocol), or other telecommunication protocols. The MDC device 100 or 500 can transfer medication container 120 information, notification of the presence or absence of a medication container 120, 600 or 600', and absolute or relative weight change of a medication container 120, 600 or 600'. Using this transferred information, the third party can determine if an error in dosage has occurred, such as the user taking too little or too much of a medication.

Similarly, the MDC device 100 or 500 contains a warning mechanism that is capable of issuing warnings using three different methods. Warning the user directly, warning a third party via the aforementioned communication methods, and asking the user to get help are all ways for the MDC device 100 or 500 to help alleviate the danger of incorrect medication doses. For example, the MDC device 100 or 500 stores how much of a particular medication has been taken; however, if this amount does not match the recommended dosage of that particular medication, which is also stored in the MDC device 100 or 500, the MDC device 100 or 500 will issue a warning. Likewise, warnings are also able to be sent back from a remote location in the form of a light or audible signal to alert the user.

Additionally, an operator or a third party can be alerted if there is a discrepancy related to the dosage of a medication. If a dosage problem exists, the operator may alert a responsible party. The third party may then call the user back to communicate in real-time. Similarly, if a prescription needs to be refilled, the MDC device 100 or 500 can alert a pharmacy. The user or the user's physician is also able to set the appropriate warning levels and communication options of the MDC device 100 or 500 to tailor the system to an individual's needs.

The MDC device 100 or 500 also includes preventative measures should a user misuse a medication. For example, if a user takes a medication too many times in a single day, the user may be locked out of the MDC device 100 or 500. Furthermore, a physician, nurse, nurse practitioner, counselor, or other qualified medical person can help a user interpret data from the MDC device 100 or 500 or answer any other questions that the user may have about the MDC device 100 or 500. A counselor or another person in a similar role is the first line of communication to relay information to and from the user of the MDC device 100 and 500.

Certain modifications and improvements will occur to those skilled in the art upon a reading of the foregoing description. By way of example, the prescription medication control system and method can be adapted for use in a commercial retail setting such as a pharmacy. The system could monitor pharmacy activities and determine whether incorrect dosages or theft has occurred. It could also be able to integrate with a pharmacy's inventory system and evaluate other problems such as drug interaction errors. In a retail setting, the system could also provide quality assurance where drugs need to be accurately dispensed.

Also, the present invention could be adapted for non-pharmaceutical environments including, but not limited to, electronics, hardware, assembly line systems, or any other setting where containers of components need to be monitored.

The website 1101 may include an on-site medical attendant or other personnel to evaluate and monitor data and other activities. The system 1100 is configured and arranged to track individual dosages dispensed daily as well as one or more courses of medication taken over time to determine compliance by the patient. The system 1100 is configured to warn patients, caregivers, and/or others of mistakes or non-compliance events which deviate from an expected dispensing scheduled for one or more medications associated with a patient. The system 1100 is configured to register and track medications from a variety of sources. For example, one or more medications for a particular patient may be provided from different sources such as different pharmacies. The system 1100 is also configured to register non-prescription or over-the-counter medications. For example, an RFID tag could be generated for a vitamin container so that the vitamin may be registered. The MDC device could be configured to receive a dispensing trigger signal from the website 1101 to initiate a dispensing sequence for the registered vitamin when the patient needs to take said vitamin.

Figure 17:
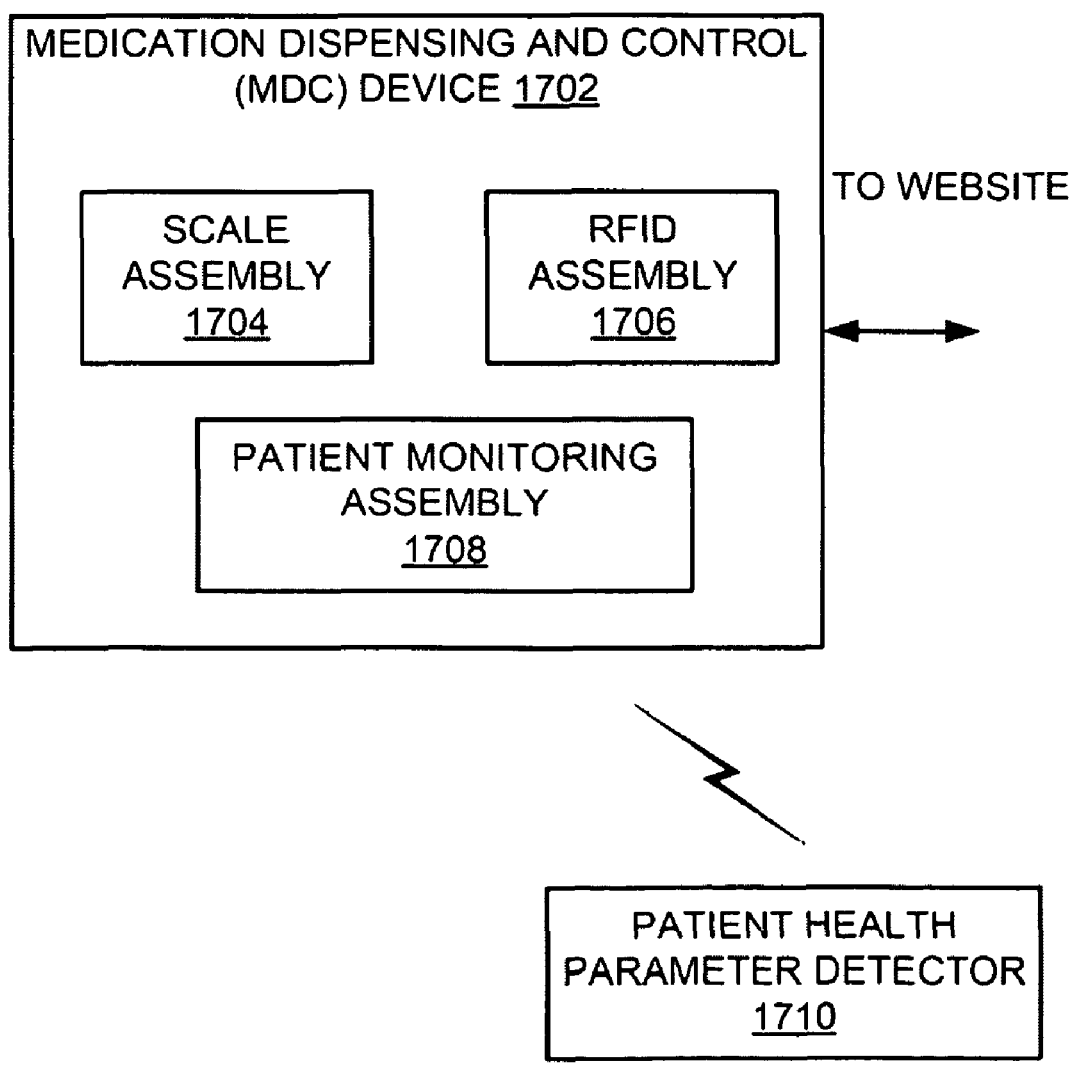
FIG. 17 is a block diagram of an in-home patient monitoring and drug compliance system, in accordance with one embodiment of the present invention.

FIG. 17 is a block diagram of an in-home patient monitoring and drug compliance system 1700. The system 1700 includes a MDC device 1702 which is similar to MDC device 100, 500 or 1106. The MDC device 1702 communicates with a website (e.g., website 1101) and includes a scale assembly 1704 and an RFID assembly 1706. However, the MDC device 1702 further includes a patient monitoring assembly 1708 to monitor one or more health parameters of the patient. The health parameters include one or more of a blood pressure detector, a temperature (or other vital sign) detector, etc. A patient health parameter detector 1710 is provided to detect or measure one or more vital signs or a health condition of a patient and communicate the measurement(s) via radio frequency (RF) or other wired or wireless communication medium to the MDC device 1702. The patient monitoring assembly 1708 would report the measurements to the website. The website would be configured to generate the necessary notification or alert in the event that a health condition is detected that requires immediate medical attention. The patient monitoring assembly 1708 may detect a medical alert signal generated from the patient health parameter detector 1710.

Figure 18:
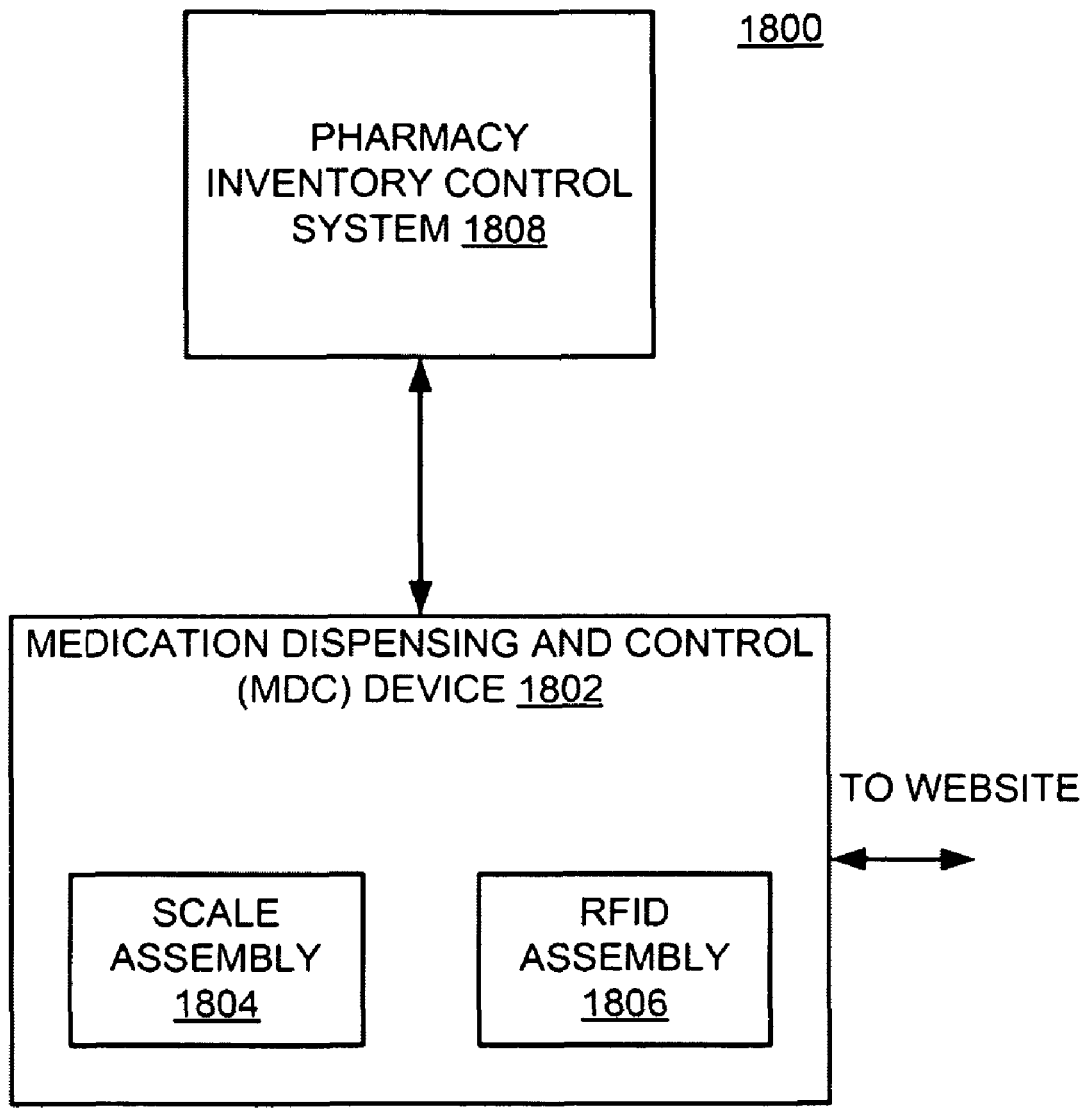
FIG. 18 is a block diagram of a pharmacy compliance system, in accordance with one embodiment of the present invention.

FIG. 18 is a block diagram of a pharmacy compliance system 1800. The pharmacy compliance system 1800 includes a medication dispensing and control (MSC) device 1802 and a pharmacy inventory control system 1808. The MDC device 1802 would weigh the medication or medication container being dispensed to fill a prescription by scale assembly 1804. For example, after the medication container is completely filled with the medication, the medication container may be weighed. This weight can also be sent to website 1101 for use by system 1100. For example, in the event a registered medication container has a weight that is not within expected limits the weight from the pharmacy compliance system 1800 could be used to detect missing dosages or an error in the filled prescription.

It is well known that prescriptions are sometimes filled erroneously. For example, the wrong medication or the wrong dosage of the proper medication may be filled in the medication container and given to the patient. As a checking and verifying mechanism, the weight from the pharmacy compliance system 1800 could be used to detect medication dispensing errors related to the prescription before the filed medication container 600 leaves the pharmacy.

The MDC device 1802 further includes an RFID assembly 1806 to read and write RFID data from and to a RFID tag. The MDC device 1802 would also communicate dispensing data to the inventory control system 1808. As medications are dispensed by filling a prescription, the inventory control system 1808 would determine when new medications need to be reordered from the manufacturer.

In exemplary embodiments, the processes may be implemented in hardware, software, firmware, or any combination thereof in a form of a computer program product comprising one or more computer-executable instructions. When implemented in software, the computer program product may be stored on or transmitted using a computer-readable medium, which includes computer storage medium and computer communication medium.

The term "computer storage medium" refers herein to any medium adapted for storing the instructions that cause the computer to execute the processes. By way of example, and not limitation, the computer storage medium may comprise solid-sate memory devices, including electronic memory devices (e.g., RAM, ROM, EEPROM, and the like), optical memory devices (e.g., compact discs (CD), digital versatile discs (DVD), and the like), or magnetic memory devices (e.g., hard drives, flash drives, tape drives, and the like), or other memory devices adapted to store the computer program product, or a combination of such memory devices.

The term "computer communication medium" refers herein to any physical interface adapted to transmit the computer program product from one place to another using for example, a modulated carrier wave, an optical signal, a DC or AC current, and the like means. By way of example, and not limitation, the computer communication medium may comprise twisted wire pairs, printed or flat cables, coaxial cables, fiber-optic cables, digital subscriber lines (DSL), or other wired, wireless, or optical serial or parallel interfaces, or a combination thereof.

The above mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the invention.

What is claimed is:

1. A medication dispensing device comprising:
   a housing having an enclosure configured to provide direct access to a current medication container storing medication to be dispensed;
   a plurality of bins, within the housing, each bin configured to receive and store therein a medication container within a bin seat; and
   a scale assembly, within the housing, configured to automatically lift the medication container from the bin seat, weigh the medication container at least once and lower the medication container into the bin seat during a weighing cycle.

2. The device according to claim 1, wherein during the weighing cycle the scale assembly lifts the medication container from the bin seat, weighs the medication container N times and then lowers the medication container into the bin seat, wherein the N is a number greater than 0.

3. The device according to claim 2, wherein the N equals 256.

4. The device according to claim 1, wherein the housing comprises a secondary dispensing lid and a primary lid; where during a dispensing cycle, the primary lid is in a locked state and the secondary dispensing lid is configured to be automatically moved to an open position.

5. The device according to claim 4, further comprising a rotatable medicine carousel, where said carousel holds the medication to be dispensed and is rotated to a dispensing position immediately below the secondary dispensing lid prior to the secondary dispensing lid being automatically opened or unlocked for medication container removal.

6. The device according to claim 5, wherein when the primary lid is open, the scale assembly is disabled and the rotatable medicine carousel is disabled from rotating.

7. The device according to claim 5, further comprising a radio frequency identification (RFID) tag reader configured to read RFID data associated with an RFID tag affixed to the medication container.

8. The device according to claim 5, further comprising a communication module configured to communicate RFID data to a website and to receive a dispensing trigger signal from the website according to a determined dispensing schedule for a medication.

9. The device according to claim 8, wherein the dispensing trigger signal identifies a respective one medication and initiates a dispensing sequence of the respective one medication from a respective one bin; and further comprising a processor configured to cause the rotatable medicine carousel to align the respective one bin with the dispensing position and to cause the secondary dispensing lid to automatically move to the open position.

10. The device according to claim 1, further comprising a sensor configured to determine the presence of the medication container being returned to or removed from the bin seat.

11. The device according to claim 1, further comprising a plurality of lock-out mechanisms configured to make available only one of said medication containers in said plurality of bins and wherein said plurality of bins are linearly arranged.

12. The device according to claim 11, wherein during the weighing cycle the scale assembly lifts the medication container from the bin seat, measures a weight of the medication container N times and then lowers the medication container into the bin seat, wherein the N is a number greater than 0.

13. The device according to claim 12, further comprising an identification technology reader configured to read data associated with an identification code affixed to the medication container.

14. The device according to claim 13, further comprising a communication module configured to communicate the data to a server and to receive a dispensing trigger signal from the server according to a determined dispensing schedule for a medication.

15. The device according to claim 14, wherein the dispensing trigger signal identifies a respective one medication and initiates a dispensing sequence of the respective one medication from a respective one bin.

16. The device according to claim 15, wherein the identification technology reader is a radio frequency identification (RFID) tag reader and the identification code is an RFID tag.

17. The device according to claim 15, wherein the identification technology reader is a bar code reader and the identification code is a bar code.

18. The device according to claim 13, wherein the identification technology reader is a bar code reader and the identification code is a bar code.

19. The device according to claim 13, wherein the identification technology reader is a radio frequency identification (RFID) tag reader and the identification code is an RFID tag.

20. The device according to claim 1, wherein during the weighing cycle the scale assembly lifts the medication container from the bin seat, records N times a measured value of a force applied by the medication container onto the scale assembly, and then lowers the medication container into the bin seat, wherein the N is a number greater than 0.

21. The device according to claim 20, wherein the N equals 256.

22. The device according to claim 1, further comprising a radio frequency identification (RFID) tag reader configured to read RFID data associated with an RFID tag affixed to the medication container.

23. The device according to claim 22, further comprising a communication module configured to communicate the RFID data to a website and to receive a dispensing trigger signal from the website according to a determined dispensing schedule for a medication.

24. The device according to claim 23, wherein the dispensing trigger signal identifies a respective one medication and initiates a dispensing sequence of the respective one medication from a respective one bin; and further comprising a processor configured to cause the rotatable medicine carousel to align the respective one bin with the dispensing position and to cause the secondary dispensing lid to automatically move to the open position.

25. The device according to claim 23, wherein said medication is stored in said medication container.

26. The device according to claim 22, further comprising a communication module configured to communicate the RFID data to a server and to receive a dispensing trigger signal from the server according to a determined dispensing schedule for a medication.

27. The device according to claim 26, wherein the dispensing trigger signal identifies a respective one medication and initiates a dispensing sequence of the respective one medication from a respective one bin; and further comprising a processor configured to cause the rotatable medicine carousel to align the respective one bin with the dispensing position and to cause the secondary dispensing lid to automatically move to the open position.

28. The device according to claim 26, wherein said medication is stored in said medication container.

29. The device according to claim 1, further comprising a communication module configured to communicate RFID data to a website and to receive a dispensing trigger signal from the website according to a determined dispensing schedule for a medication.

30. The device according to claim 29, wherein said medication is stored in said medication container.

31. The device according to claim 1, further comprising a communication module configured to communicate RFID data to a server and to receive a dispensing trigger signal from the server according to a determined dispensing schedule for a medication.

32. The device according to claim 31, wherein said medication is stored in said medication container.

33. The device according to claim 1, further comprising an identification technology reader configured to read data associated with an identification code affixed to the medication container.

34. The device according to claim 33, wherein the identification technology reader is a bar code reader and the identification code is a bar code.

35. The device according to claim 34, further comprising a communication module configured to communicate the data to a website and to receive a dispensing trigger signal from the website according to a determined dispensing schedule for a medication.

36. The device according to claim 35, wherein the dispensing trigger signal identifies a respective one medication and initiates a dispensing sequence of the respective one medication from a respective one bin; and further comprising a processor configured to cause the rotatable medicine carousel to align the respective one bin with the dispensing position and to cause the secondary dispensing lid to automatically move to the open position.

37. The device according to claim 35, wherein said medication is stored in said medication container.

38. The device according to claim 33, further comprising a communication module configured to communicate the data to a website and to receive a dispensing trigger signal from the website according to a determined dispensing schedule for a medication.

39. The device according to claim 38, wherein the dispensing trigger signal identifies a respective one medication and initiates a dispensing sequence of the respective one medication from a respective one bin; and further comprising a processor configured to cause the rotatable medicine carousel to align the respective one bin with the dispensing position and to cause the secondary dispensing lid to automatically move to the open position.

40. The device according to claim 38, wherein said medication is stored in said medication container.

41. The device according to claim 1, further comprising an identification technology reader configured to read data associated with an identification code affixed to the medication container.

42. The device according to claim 41, wherein the identification technology reader is a bar code reader and the identification code is a bar code.

43. The device according to claim 42, further comprising a communication module configured to communicate said data to a website and to receive a dispensing trigger signal from the website according to a determined dispensing schedule for a medication.

44. The device according to claim 43, wherein the dispensing trigger signal identifies a respective one medication and initiates a dispensing sequence of the respective one medication from a respective one bin; and further comprising a processor configured to cause the rotatable medicine carousel to align the respective one bin with the dispensing position and to cause the secondary dispensing lid to automatically move to the open position.

45. The device according to claim 43, wherein said medication is stored in said medication container.

46. The device according to claim 42, further comprising a communication module configured to communicate the data to a server and to receive a dispensing trigger signal from the server according to a determined dispensing schedule for a medication.

47. The device according to claim 46, wherein the dispensing trigger signal identifies a respective one medication and initiates a dispensing sequence of the respective one medication from a respective one bin; and further comprising a processor configured to cause the rotatable medicine carousel to align the respective one bin with the dispensing position and to cause the secondary dispensing lid to automatically move to the open position.

48. The device according to claim 41, further comprising a communication module configured to communicate said data to a website and to receive a dispensing trigger signal from the website according to a determined dispensing schedule for a medication.

49. The device according to claim 48, wherein the dispensing trigger signal identifies a respective one medication and initiates a dispensing sequence of the respective one medication from a respective one bin; and further comprising a processor configured to cause the rotatable medicine carousel to align the respective one bin with the dispensing position and to cause the secondary dispensing lid to automatically move to the open position.

50. The device according to claim 48, wherein said medication is stored in said medication container.

51. The device according to claim 41, further comprising a communication module configured to communicate the data to a server and to receive a dispensing trigger signal from the server according to a determined dispensing schedule for a medication.

52. The device according to claim 51, wherein the dispensing trigger signal identifies a respective one medication and initiates a dispensing sequence of the respective one medication from a respective one bin; and further comprising a processor configured to cause the rotatable medicine carousel to align the respective one bin with the dispensing position and to cause the secondary dispensing lid to automatically move to the open position.

53. The device according to claim 46, wherein said medication is stored in said medication container.

54. The device according to claim 51, wherein said medication is stored in said medication container.

55. The device according to claim 1, further comprising a communications module and a pharmacy inventory control system, said communications module configured to communicate medication data to the pharmacy inventory control system.

56. The system according to claim 55, wherein said pharmacy inventory control system determines when new medications need to be ordered.

57. The system according to claim 55, wherein said pharmacy inventory control system has the capability to detect medication dispensing errors.

58. A medication dispensing device comprising:
means for removably storing serially one or more medication containers;
means for housing the storing means; and
means for automatically lifting a respective one medication container from the storing means, weighing the respective one medication container at least once and lowering the respective one medication container into the storing means during a weighing cycle.

59. The device according to claim 58, wherein during the weighing cycle, the weighing means includes means for weighing the medication container N times wherein the N is a number greater than 0.

60. The device according to claim 59, wherein a value of the N equals 256.

61. The device according to claim 58, wherein the housing means includes a primary lid and a secondary dispensing lid; and further comprising means for unlocking the secondary dispensing lid automatically wherein during a dispensing cycle, the primary lid is in a locked state; and the secondary dispensing lid is configured to be automatically moved to an open position or manually open.

62. The device according to claim 61, further comprising a means for rotating the storing means; and means for aligning the respective one medication container with a dispensing position immediately below the secondary dispensing lid prior to automatically moving the secondary dispensing lid to the open position or allowing the dispensing lid to be opened.

63. The device according to claim 62, wherein when the primary lid is open, the lifting, weighing and lowering means are disabled and the rotating means is disabled.

64. The device according to claim 62, further comprising means for reading a radio frequency identification (RFID) data associated with an RFID tag affixed to the respective one medication container.

65. The device according to claim 62, further comprising means for communicating RFID data to a website; and means for receiving a dispensing trigger signal from the website according to a determined dispensing schedule for a respective one medication.

66. The device according to claim 65, wherein the dispensing trigger signal identifies a respective one medication being stored and initiates a dispensing sequence.

67. The device according to claim 65, wherein said respective one medication is stored in at least one of said medication containers.

68. The device according to claim 62, further comprising means for communicating RFID data to a server; and means for receiving a dispensing trigger signal from the server according to a determined dispensing schedule for a respective one medication.

69. The device according to claim 68, wherein the dispensing trigger signal identifies a respective one medication being stored and initiates a dispensing sequence.

70. The device according to claim 68, wherein the dispensing trigger signal identifies a respective one medication being stored and initiates a dispensing sequence.

71. The device according to claim 68, wherein said respective one medication is stored in at least one of said medication containers.

72. The device according to claim 58, further comprising means for sensing a presence of the respective one medication container being returned to or removed from the storing means.

73. The device according to claim 58, further comprising means for making only one medication container available at a particular time, and wherein said storing means comprises means for linearly storing said one or more medication containers.

74. The device according to claim 73, wherein during the weighing cycle, the weighing means includes means for measuring the weight of the medication container N times, wherein the N is a number greater than 0.

75. The device according to claim 74, further comprising means for reading data associated with an identification code affixed to the respective one medication container.

76. The device according to claim 75, further comprising means for communicating the data to a server; and means for receiving a dispensing trigger signal from the server according to a determined dispensing schedule for a respective one medication.

77. The device according to claim 76, wherein the dispensing trigger signal identifies a respective one medication being stored and initiates a dispensing sequence.

78. The device according to claim 77, wherein the means for reading data is a means for reading a radio frequency identification (RFID) data associated with an RFID tag affixed to the respective one medication container.

79. The device according to claim 77, wherein the means for reading data is a means for reading bar code data associated with a bar code affixed to the respective one medication container.

80. The device according to claim 75, wherein the means for reading data is a means for reading a radio frequency identification (RFID) data associated with an RFID tag affixed to the respective one medication container.

81. The device according to claim 75, wherein the means for reading data is a means for reading bar code data associated with a bar code affixed to the respective one medication container.

82. The device according to claim 58, wherein during the weighing cycle, the lifting, weighing and lowering means includes means for lifting the respective one medication container from the bin seat, recording N times a measured value of a force applied by the respective one medication container onto the weighing means, and then lowering the respective one medication container back into the bin seat, wherein the N is a number greater than 0.

83. The device according to claim 82, wherein a value of the N equals 256.

84. The device according to claim 58, further comprising means for reading a radio frequency identification (RFID) data associated with an RFID tag affixed to the respective one medication container.

85. The device according to claim 84, further comprising means for communicating the RFID data to a website; and means for receiving a dispensing trigger signal from the website according to a determined dispensing schedule for a respective one medication.

86. The device according to claim 85, wherein the dispensing trigger signal identifies a respective one medication being stored and initiates a dispensing sequence.

87. The device according to claim 85, wherein said respective one medication is stored in at least one of said medication containers.

88. The device according to claim 84, further comprising means for communicating the RFID data to a server; and means for receiving a dispensing trigger signal from the server according to a determined dispensing schedule for a respective one medication.

89. The device according to claim 88, wherein the dispensing trigger signal identifies a respective one medication being stored and initiates a dispensing sequence.

90. The device according to claim 88, wherein said respective one medication is stored in at least one of said medication containers.

91. The device according to claim 58, further comprising means for reading data associated with an identification code affixed to the respective one medication container.

92. The device according to claim 91, wherein the identification code is a bar code.

93. The device according to claim 92, further comprising means for communicating said data to a website; and means for receiving a dispensing trigger signal from the website according to a determined dispensing schedule for a respective one medication.

94. The device according to claim 93, wherein the dispensing trigger signal identifies a respective one medication being stored and initiates a dispensing sequence.

95. The device according to claim 93, wherein said respective one medication is stored in at least one of said medication containers.

96. The device according to claim 91, further comprising means for communicating said data to a website; and means for receiving a dispensing trigger signal from the website according to a determined dispensing schedule for a respective one medication.

97. The device according to claim 96, wherein the dispensing trigger signal identifies a respective one medication being stored and initiates a dispensing sequence.

98. The device according to claim 96, wherein said respective one medication is stored in at least one of said medication containers.

99. The device according to claim 58, further comprising means for reading data associated with an identification code affixed to the respective one medication container.

100. The device according to claim 99, wherein the identification code is a bar code.

101. The device according to claim 100, further comprising means for communicating said data to a server; and means for receiving a dispensing trigger signal from the server according to a determined dispensing schedule for a respective one medication.

102. The device according to claim 101, wherein the dispensing trigger signal identifies a respective one medication being stored and initiates a dispensing sequence.

103. The device according to claim 101, wherein the dispensing trigger signal identifies a respective one medication being stored and initiates a dispensing sequence.

104. The device according to claim 101, wherein said respective one medication is stored in at least one of said medication containers.

105. The device according to claim 100, further comprising means for communicating said data to a server; and means for receiving a dispensing trigger signal from the server according to a determined dispensing schedule for a respective one medication.

106. The device according to claim 105, wherein the dispensing trigger signal identifies a respective one medication being stored and initiates a dispensing sequence.

107. The device according to claim 105, wherein said respective one medication is stored in at least one of said medication containers.

108. The device according to claim 100, further comprising means for communicating said data to a website; and means for receiving a dispensing trigger signal from the website according to a determined dispensing schedule for a respective one medication.

109. The device according to claim 108, wherein the dispensing trigger signal identifies a respective one medication being stored and initiates a dispensing sequence.

110. The device according to claim 108, wherein said respective one medication is stored in at least one of said medication containers.

111. The device according to claim 99, further comprising means for communicating said data to a server; and means for receiving a dispensing trigger signal from the server according to a determined dispensing schedule for a respective one medication.

112. The device according to claim 111, wherein the dispensing trigger signal identifies a respective one medication being stored and initiates a dispensing sequence.

113. The device according to claim 111, wherein the dispensing trigger signal identifies a respective one medication being stored and initiates a dispensing sequence.

114. The device according to claim 111, wherein said respective one medication is stored in at least one of said medication containers.

115. The device according to claim 99, further comprising means for communicating said data to a website; and means for receiving a dispensing trigger signal from the website according to a determined dispensing schedule for a respective one medication.

116. The device according to claim 115, wherein the dispensing trigger signal identifies a respective one medication being stored and initiates a dispensing sequence.

117. The device according to claim 115, wherein said respective one medication is stored in at least one of said medication containers.

118. The device according to claim 99, further comprising means for communicating said data to a server; and means for receiving a dispensing trigger signal from the server according to a determined dispensing schedule for a respective one medication.

119. The device according to claim 118, wherein the dispensing trigger signal identifies a respective one medication being stored and initiates a dispensing sequence.

120. The device according to claim 118, wherein said respective one medication is stored in at least one of said medication containers.

121. The device according to claim 58, further comprising means for communicating data to a server; and means for receiving a dispensing trigger signal from the server according to a determined dispensing schedule for a respective one medication.

122. The device according to claim 121, wherein the dispensing trigger signal identifies a respective one medication being stored and initiates a dispensing sequence.

123. The device according to claim 121, wherein the dispensing trigger signal identifies a respective one medication being stored and initiates a dispensing sequence.

124. The device according to claim 121, wherein said respective one medication is stored in at least one of said medication containers.

125. The device according to claim 58, wherein the housing means includes a primary means for lidding and a secondary means for lidding and dispensing; and further comprising means for unlocking the secondary means for lidding and dispensing automatically wherein during a dispensing cycle, the primary means for lidding is in a locked state; and the secondary means for lidding and dispensing is configured to be automatically moved to an open position or manually open.

126. The device according to claim 125, further comprising a means for rotating the storing means; and means for aligning the respective one medication container with a dispensing position immediately below the secondary means for lidding and dispensing prior to automatically moving the secondary means for lidding and dispensing to the open position or allowing the secondary means for lidding and dispensing to be opened.

127. The device according to claim 126, wherein when the primary means for lidding is open, the lifting, weighing and lowering means are disabled and the rotating means is disabled.

128. The device according to claim 58, further comprising means for communicating data to a website; and means for receiving a dispensing trigger signal from the website according to a determined dispensing schedule for a respective one medication.

129. The device according to claim 128, wherein the dispensing trigger signal identifies a respective one medication being stored and initiates a dispensing sequence.

130. The device according to claim 128, wherein said respective one medication is stored in at least one of said medication containers.

131. A method of controlling medication dispensation comprising:
storing serially one or more medication containers in one or more bins in a secure housing;
automatically lifting a respective one medication container;
automatically weighing the respective one medication container at least once during a weighing cycle;
automatically lowering the respective one medication container into a bin seat.

132. The method according to claim 131, wherein the weighing cycle includes weighing the respective one medication container N times and lowering the respective one medication container into the bin seat, wherein the N is a number greater than 0.

133. The method according to claim 132, wherein a value of the N equals 256.

134. The method according to claim 131, further comprising unlocking a secondary dispensing lid automatically during a dispensing cycle.

135. The method according to claim 131, further comprising reading a radio frequency identification (RFID) data associated with an RFID tag affixed to the respective one medication container.

136. The method according to claim 135, further comprising communicating the RFID data to a website; and receiving a dispensing trigger signal from the website according to a determined dispensing schedule for a respective one medication.

137. The method according to claim 136, wherein the dispensing trigger signal identifies the respective one medication in a respective one bin; and further comprising aligning the respective one bin to a dispensing position and automatically opening a dispensing lid.

138. The method according to claim 135, further comprising communicating the RFID data to a server; and receiving a dispensing trigger signal from the server according to a determined dispensing schedule for a respective one medication.

139. The method according to claim 138, wherein the dispensing trigger signal identifies the respective one medication in a respective one bin; and further comprising aligning the respective one bin to a dispensing position and automatically opening a dispensing lid.

140. The method according to claim 131, further comprising sensing a presence of the respective one medication container being returned to or removed from the bin seat.

141. The method according to claim 131, wherein the weighing cycle includes recording N times a measured value of a force applied by the medication container onto a scale assembly and lowering the respective one medication container into the bin seat, wherein the N is a number greater than 0.

142. The method according to claim 131, further comprising reading data associated with an identification code affixed to the respective one medication container.

143. The method according to claim 142, wherein the identification code is a bar code.

144. The method according to claim 143, further comprising communicating the data to a website; and receiving a dispensing trigger signal from the website according to a determined dispensing schedule for a respective one medication.

145. The method according to claim 144, wherein the dispensing trigger signal identifies the respective one medication in a respective one bin; and further comprising aligning the respective one bin to a dispensing position and automatically opening a dispensing lid.

146. The method according to claim 142, further comprising communicating the data to a website; and receiving a dispensing trigger signal from the website according to a determined dispensing schedule for a respective one medication.

147. The method according to claim 146, wherein the dispensing trigger signal identifies the respective one medication in a respective one bin; and further comprising aligning the respective one bin to a dispensing position and automatically opening a dispensing lid.

148. The method according to claim 131, further comprising reading data associated with an identification code affixed to the respective one medication container.

149. The method according to claim 148, wherein the identification code is a bar code.

150. The method according to claim 149, further comprising communicating the data to a server; and receiving a dispensing trigger signal from the server according to a determined dispensing schedule for a respective one medication.

151. The method according to claim 150, wherein the dispensing trigger signal identifies the respective one medication in a respective one bin; and further comprising aligning the respective one bin to a dispensing position and automatically opening a dispensing lid.

152. The method according to claim 148, further comprising communicating the data to a server; and receiving a dispensing trigger signal from the server according to a determined dispensing schedule for a respective one medication.

153. The method according to claim 152, wherein the dispensing trigger signal identifies the respective one medication in a respective one bin; and further comprising aligning the respective one bin to a dispensing position and automatically opening a dispensing lid.

154. A system for dispensing medications comprising:
a plurality of in-home medication dispensing and control (MDC) devices, each MDC device having a secure and locked housing configured to store therein a plurality of registered medication containers in discrete bin locations, and a scale assembly configured to weigh one registered medication container at a time; and
a server configured to register and track an amount of medication taken based on a weight generated by the scale assembly for each registered medication container associated with each MDC device,
wherein the secure housing includes an enclosure with a lid, the lid being configured to provide direct access to a current registered medication container storing medication to be dispensed; and the scale assembly, within the housing, configured to automatically lift at least one of the plurality of registered medication containers from a bin seat of a bin, weigh the at least one of the plurality of registered medication containers at least once and lower the at least one of the plurality of registered medication containers into the bin seat during a weighing cycle.

155. The system according to claim 154, wherein during the weighing cycle the scale assembly weighs the at least one of the plurality of registered medication containers N times, wherein the N is a number greater than 0.

156. The system according to claim 155, wherein a value of the N equals 256.

157. The system according to claim 155, further comprising a sensor configured to determine a presence of the at least one of the plurality of registered medication containers being returned to or removed from the bin seat.

158. The system according to claim 155, wherein the server is configured to detect non-compliance consumption of dispensed medication and to report the non-compliance consumption to a third party.

159. The system according to claim 155, wherein the server is configured to track activity associated with each MDC device in an administration mode and a dispensing mode.

160. The system according to claim 155, wherein the server is configured to generate an alert when an overdosage condition is detected wherein the overdosage condition is determined based on the tracked weight for any one registered medication.

161. The system according to claim 154, wherein the server is configured to generate a refill order associated with one or more of the registered medication containers to one or more pharmacies.

162. The system according to claim 155, wherein the server is configured to detect non-compliance consumption of dispensed medication and to report the non-compliance consumption to a patient.

163. The system according to claim 154, wherein the lid is a primary lid and which further comprises a secondary dispensing lid; and during a dispensing cycle, the primary lid is in a locked state; and the secondary dispensing lid is configured to be automatically moved to an open position or to be unlocked.

164. The system according to claim 163, wherein the MDC device further comprises a rotatable medicine carousel of the discrete bin locations, the carousel being configured to be rotated to a dispensing position immediately below the secondary dispensing lid prior to the secondary dispensing lid being automatically unlocked or moved to the open position.

165. The system according to claim 164, wherein when the primary lid is open, the scale assembly is disabled and the rotatable medicine carousel is disabled from rotating.

166. The system according to claim 164, wherein the MDC device further comprises a radio frequency identification (RFID) tag reader configured to read RFID data associated with an RFID tag affixed to the at least one of the plurality of registered medication containers.

167. The system according to claim 164, further comprising a communication module configured to communicate RFID data to a website and to receive a dispensing trigger signal from the website according to a determined dispensing schedule for a registered medication and secondary dispensing lid being controlled in response to the dispensing trigger signal.

168. The system according to claim 167, wherein the dispensing trigger signal identifies a respective one medication and initiates a dispensing sequence of the respective one medication from a respective one bin; and further comprising a processor configured to cause the rotatable medicine carousel to align the respective one bin to the dispensing position and to cause the secondary dispensing lid to be automatically unlocked or moved to the open position.

169. The system according to claim 164, further comprising a communication module configured to communicate RFID data to said server and to receive a dispensing trigger signal from said server according to a determined dispensing schedule for a registered medication and secondary dispensing lid being controlled in response to the dispensing trigger signal.

170. The system according to claim 154, wherein the server is configured to generate an alert when an overdosage condition is detected wherein the overdosage condition is determined based on the tracked weight for any one registered medication.

171. The system according to claim 154, wherein the server is configured to generate a refill order associated with one or more of the registered medication containers to one or more pharmacies.

172. The system according to claim 154, wherein said discrete bin locations are arranged linearly.

173. The system according to claim 172, wherein during the weighing cycle the scale assembly measures the weight of at least one of the plurality of registered medication containers N times, wherein the N is a number greater than 0.

174. The system according to claim 173, wherein the MDC device further comprises an identification technology reader configured to read data associated with an identification code affixed to the at least one of the plurality of registered medication containers.

175. The system according to claim 174, further comprising a communication module configured to communicate the data to a server and to receive a dispensing trigger signal from the server according to a determined dispensing schedule for a registered medication.

176. The system according to claim 175, wherein the dispensing trigger signal identifies a respective one medication and initiates a dispensing sequence of the respective one medication from a respective one bin.

177. The system according to claim 176, wherein the identification technology reader is a radio frequency identification (RFID) tag reader and the identification code is an RFID tag.

178. The system according to claim 176, wherein the identification technology reader is a bar code reader and the identification code is a bar code.

179. The system according to claim 174, wherein the identification technology reader is a radio frequency identification (RFID) tag reader and the identification code is an RFID tag.

180. The system according to claim 174, wherein the identification technology reader is a bar code reader and the identification code is a bar code.

181. The system according to claim 154, wherein the MDC device further comprises an identification technology reader configured to read data associated with an identification code affixed to the at least one of the plurality of registered medication containers.

182. The system according to claim 155, wherein the MDC device further comprises a radio frequency identification (RFID) tag reader configured to read RFID data associated with an RFID tag affixed to the at least one of the plurality of registered medication containers.

183. The system according to claim 182, wherein the identification technology reader is a bar code reader and the identification code is a bar code.

184. The system according to claim 183, further comprising a communication module configured to communicate the data to a website and to receive a dispensing trigger signal from the website according to a determined dispensing schedule for a registered medication and secondary dispensing lid being controlled in response to the dispensing trigger signal.

185. The system according to claim 183, wherein the dispensing trigger signal identifies a respective one medication and initiates a dispensing sequence of the respective one medication from a respective one bin; and further comprising a processor configured to cause the rotatable medicine carousel to align the respective one bin to the dispensing position and to cause the secondary dispensing lid to be automatically unlocked or moved to the open position.

186. The system according to claim 182, further comprising a communication module configured to communicate the data to a website and to receive a dispensing trigger signal from the website according to a determined dispensing schedule for a registered medication and secondary dispensing lid being controlled in response to the dispensing trigger signal.

187. The system according to claim 182, wherein the dispensing trigger signal identifies a respective one medication and initiates a dispensing sequence of the respective one medication from a respective one bin; and further comprising a processor configured to cause the rotatable medicine carousel to align the respective one bin to the dispensing position and to cause the secondary dispensing lid to be automatically unlocked or moved to the open position.

188. The system according to claim 154, wherein the MDC device further comprises an identification technology reader configured to read data associated with an identification code affixed to the at least one of the plurality of registered medication containers.

189. The system according to claim 188, wherein the identification technology reader is a bar code reader and the identification code is a bar code.

190. The system according to claim 189, further comprising a communication module configured to communicate said data to a website and to receive a dispensing trigger signal from the website according to a determined dispensing schedule for a registered medication and secondary dispensing lid being controlled in response to the dispensing trigger signal.

191. The system according to claim 189, further comprising a communication module configured to communicate said data to said server and to receive a dispensing trigger signal from said server according to a determined dispensing schedule for a registered medication and secondary dispensing lid being controlled in response to the dispensing trigger signal.

192. The system according to claim 188, further comprising a communication module configured to communicate said data to a website and to receive a dispensing trigger signal from the website according to a determined dispensing schedule for a registered medication and secondary dispensing lid being controlled in response to the dispensing trigger signal.

193. The system according to claim 188, further comprising a communication module configured to communicate said data to said server and to receive a dispensing trigger signal from said server according to a determined dispensing schedule for a registered medication and secondary dispensing lid being controlled in response to the dispensing trigger signal.

194. The system according to claim 155, further comprising a communication module configured to communicate data to a website and to receive a dispensing trigger signal from the website according to a determined dispensing schedule for a registered medication and secondary dispensing lid being controlled in response to the dispensing trigger signal.

195. The system according to claim 154, further comprising a communication module configured to communicate data to said server and to receive a dispensing trigger signal from said server according to a determined dispensing schedule for a registered medication and secondary dispensing lid being controlled in response to the dispensing trigger signal.

* * * * *